United States Patent
Overall et al.

(10) Patent No.: US 7,445,605 B2
(45) Date of Patent: Nov. 4, 2008

(54) DETECTION OF APEX MOTION FOR MONITORING CARDIAC DYSFUNCTION

(75) Inventors: William Ryan Overall, Palo Alto, CA (US); Daniel Francis, Los Altos, CA (US); Aimee Brigitte Angel, Atherton, CA (US); R. Hardwin Mead, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/394,449

(22) Filed: Mar. 30, 2006

(65) Prior Publication Data

US 2007/0032749 A1    Feb. 8, 2007

Related U.S. Application Data

(63) Continuation-in-part of application No. 10/769,405, filed on Jan. 30, 2004, now abandoned.

(60) Provisional application No. 60/473,061, filed on May 23, 2003, provisional application No. 60/443,938, filed on Jan. 31, 2003.

(51) Int. Cl.
*A61B 5/103* (2006.01)
*A61B 5/02* (2006.01)
*A61N 1/00* (2006.01)

(52) U.S. Cl. .................. 600/595; 600/483; 600/527; 600/587; 607/17; 607/19

(58) Field of Classification Search ................. 600/595, 600/587, 508, 481, 483, 527; 607/9, 17–19
See application file for complete search history.

(56) References Cited

U.S. PATENT DOCUMENTS

| 4,917,115 | A | 4/1990 | Flammang |
| 5,404,877 | A | 4/1995 | Nolan |
| 5,693,075 | A | 12/1997 | Plicchi et al. |
| 5,899,927 | A | 5/1999 | Ecker et al. |
| 6,009,349 | A | 12/1999 | Mouchawar |
| 6,141,588 | A | 10/2000 | Cox et al. |
| 6,501,983 | B1 | 12/2002 | Natarajan et al. |
| 6,595,933 | B2 * | 7/2003 | Sarvazyan et al. ........... 600/587 |
| 2003/0158492 | A1 * | 8/2003 | Sheldon et al. ............. 600/508 |

FOREIGN PATENT DOCUMENTS

| WO | WO03020366 | 3/2003 |
| WO | WO03061473 | 7/2003 |

* cited by examiner

*Primary Examiner*—Max Hindenburg
*Assistant Examiner*—H. Q. Nguyen
(74) *Attorney, Agent, or Firm*—Bozicevic, Field & Francis LLP; Pamela J. Sherwood

(57) ABSTRACT

Systems, devices and methods for detecting and monitoring cardiac dysfunction. The devices include motion sensors for detecting signals representative of the total movement of the heart, and of the apex of the heart in particular.

14 Claims, 12 Drawing Sheets

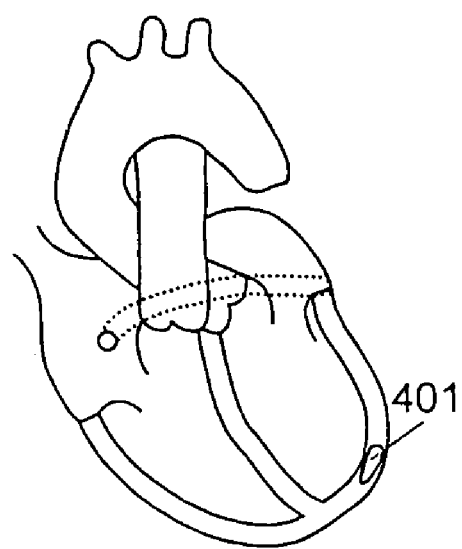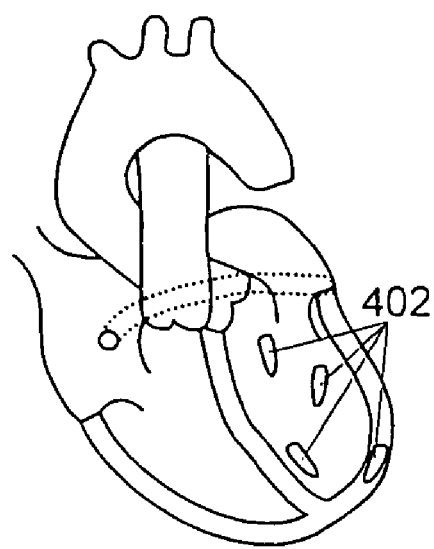
Fig. 4(a)   Fig. 4(b)
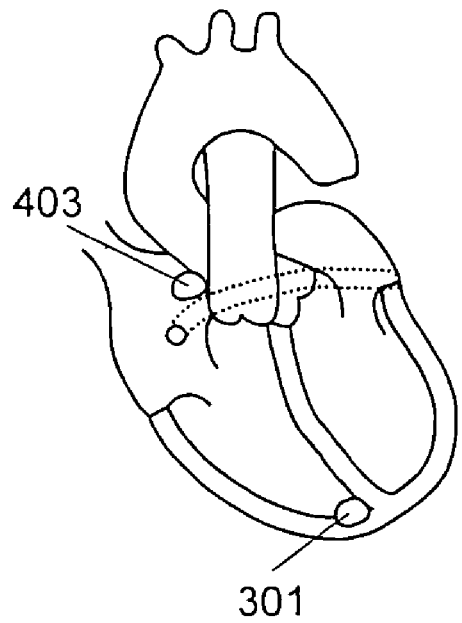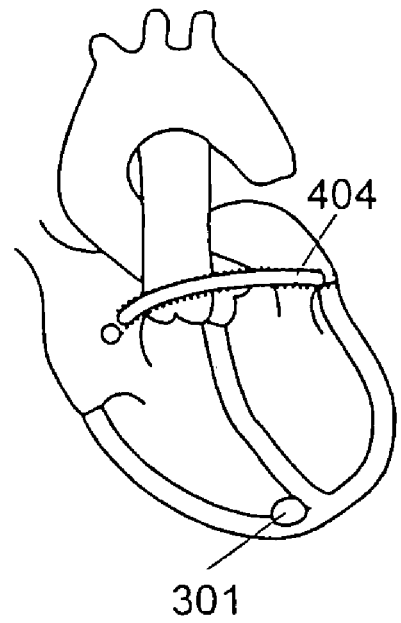
Fig. 4(c)   Fig. 4(d)

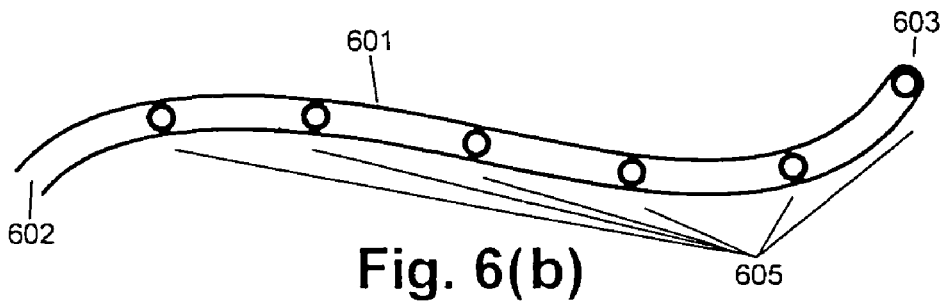
Fig. 6(b)
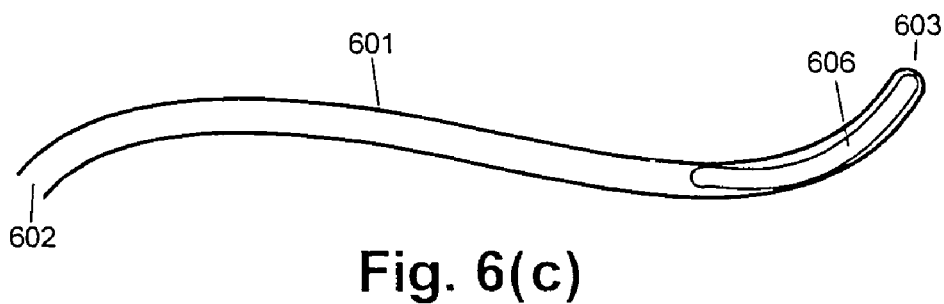
Fig. 6(c)
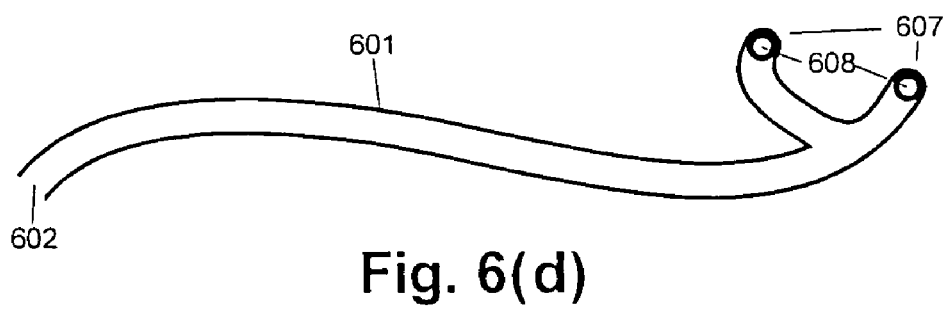
Fig. 6(d)
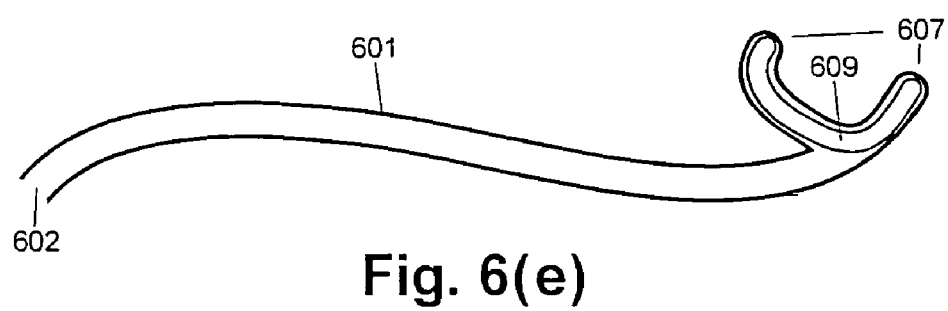
Fig. 6(e)
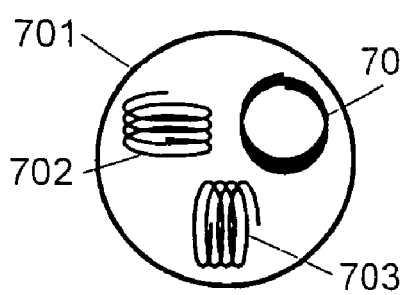  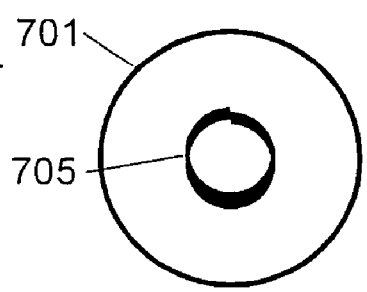
Fig. 7(a)   Fig. 7(b)

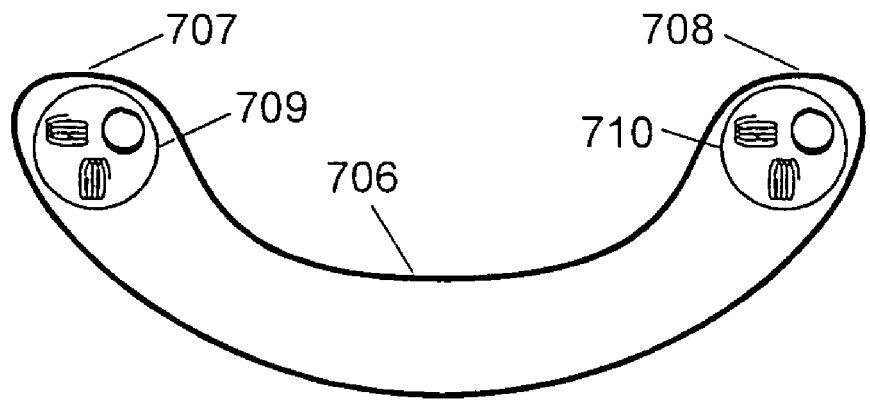
Fig. 7(c)
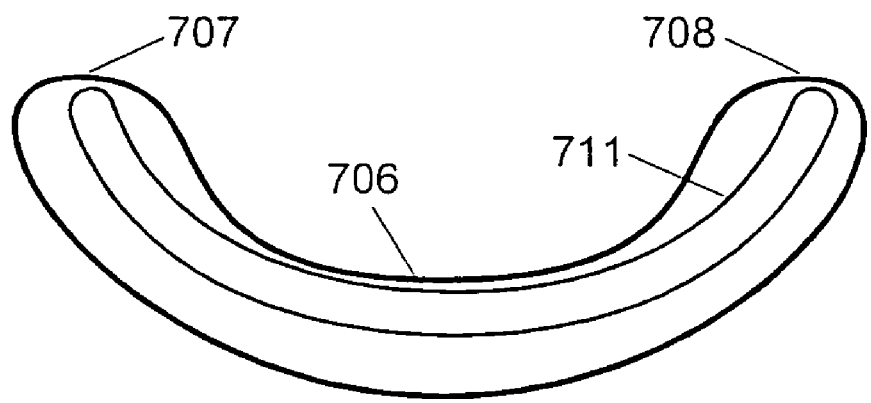
Fig. 7(d)
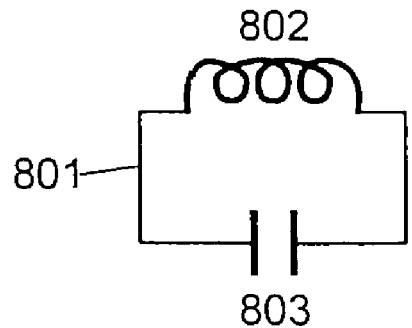 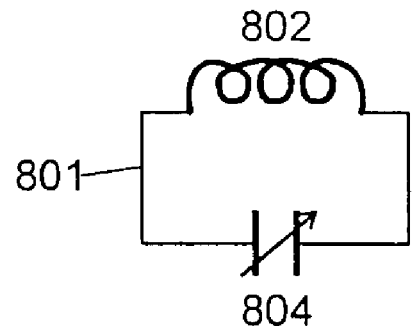
Fig. 8(a)  Fig. 8(b)

DETECTION OF APEX MOTION FOR MONITORING CARDIAC DYSFUNCTION

CROSS-REFERENCE TO RELATED APPLICATIONS

This application is a continuation-in-part of U.S. Publication No. 2004/0260346, filed Jan. 30, 2004, and claims the benefit of U.S. Provisional Application No. 60/443,938, filed Jan. 31, 2003 and U.S. Provisional Application No. 60/473,061, filed May 23, 2003, each of which is incorporated herein in their entireties.

FIELD OF THE INVENTION

This invention relates to the field of cardiac dysfunction and more specifically to methods and devices for detection and monitoring of myocardial ischemia, cardiac arrhythmias, symptoms of congestive heart failure, and other dysfunction in the heart's activity, and methods and devices for delivery of said detection and/or monitoring devices.

BACKGROUND

Coronary artery disease, in which the arteries feeding the heart narrow over time, can lead to any of a number of cardiac dysfunctions. If the narrowing prevents the heart muscle from receiving the amount of blood that it needs, a condition known as myocardial ischemia exists. Ischemia can occur during exercise, when the heart muscle's oxygen demand is greatest, or it may occur at rest. If allowed to persist, ischemia leads to heart muscle death. The primary symptom of ischemia is chest pain, or angina, although more than a third of ischemia sufferers may not experience this classic symptom (a condition known as silent ischemia).

Another cause of ischemia is myocardial infarction (MI), which occurs when an artery feeding the heart suddenly becomes blocked. This leads to acute ischemia (as opposed to the chronic ischemia usually associated with the more slow-acting processes of coronary artery disease). If left untreated, ischemia leads to myocardial cell death, or necrosis.

When an infarction is diagnosed, possible therapies include interventional catheterization (including angioplasty and/or stenting to mechanically reopen the blocked vessel) and administration of thrombolytic drugs (such as streptokinase, urokinase, or TPA). If therapy is initiated within the first thirty minutes after an MI, 100% of the myocardium can be saved. After thirty minutes, the proportion of salvageable myocardium decreases rapidly. Treatment within the first 70 minutes has also been associated with a significant decrease in in-hospital mortality.

One important component of the delay between onset of ischemia and treatment is the delay from the patient's initial symptoms until the time that he or she seeks medical assistance. In one retrospective study of heart attack survivors, only 25% contacted medical help within the first hour after onset of symptoms; 40% waited more than four hours. These patients delayed primarily because they believed that symptoms would go away or that the symptoms were not serious. Another important group of MI sufferers is the 33% (according to one study) who do not experience the classic symptom of chest pain. These patients are less likely to seek medical attention, and if they do, they may be treated less aggressively.

A large number of acute-MI patients have had previous hospitalizations for heart-related problems. Conversely, a significant number of patients who undergo catheterizations as a result of an MI will have a recurrent event within one year. As many as half of intracardiac defibrillator (ICD) recipients will have an MI within 5 years of its implantation.

The tissue death associated with infarction can lead to a number of other heart dysfunctions. If the infarction causes a disruption in the electrical conduction pathway of the heart (used to initiate its muscular contraction), then various heart rhythm abnormalities, or arrhythmias, can result. These arrhythmias can be fatal if they are not corrected quickly, so implantable therapies such as ICDs are often used to continuously monitor and treat these patients. These solutions place leads in some subset of the ventricle, atrium, or cardiac veins in order to sense and distribute electrical energy in the right atrium and both ventricles.

If the infarction reduces the pumping ability of the heart, then the heart may remodel to compensate; this remodeling can lead to a degenerative state known as heart failure. Heart failure can also be precipitated by other factors, including valvular heart disease and cardiomyopathy. Pumping ability is usually indicated by a reduced ejection fraction, the percentage of the ventricle's full volume that is delivered to the body in a single cycle. Treatment of reduced pumping ability can be pharmacologic, or ventricular assist devices (VADs) can be implanted for pumping support. In certain cases, heart transplantation may be used to repair an ailing heart.

When patients arrive at the hospital with symptoms consistent with heart disease, they may undergo any of a number of conventional diagnostic tests. The lack of accuracy of these tests, and the time required for their use, further contribute to the total time between the onset of symptoms and the initiation of therapy. These tests can be broken into four broad categories based on the type of parameter measured: chemical, hemodynamic, electrical, or mechanical.

Chemical tests measure biochemical markers in the patient's bloodstream that appear or change in concentration preferentially after myocardial cell death. Examples of such markers include creatine kinase, CK-MB, lactate dehydrogenase (LDH), troponin I & T, and myoglobin. These markers are useful in the diagnosis of acute MI because they begin to rise in concentration three to six hours after ischemia begins, and fall back to baseline values within a few days.

Hemodynamic testing involves the determination of local blood flow or pressure in the heart's chambers and vessels. Changes in chamber pressure waveforms over the cardiac cycle can indicate valvular dysfunction or heart failure. These measurements are typically made by inserting a catheter into the location to be monitored.

Electrical testing involves some measurement of the electrical conduction within the heart, typically accomplished with an electrocardiogram (EKG). EKGs are typically collected through a number of patch electrodes attached to the patient's skin. Many heart dysfunctions manifest themselves on the EKG, though some cause more subtle changes than others. Arrhythmias can be diagnosed on the EKG, as long as the EKG equipment recorded the arrhythmic event. Various changes in the EKG pattern can indicate different stages and degrees of infarction. For example, elevation or depression in the ST segment of the waveform is often associated with acute ischemia (present in the early stages of acute myocardial infarction). EKG recording from a number of electrodes placed at various locations on the body can be used to localize the region of ischemic muscle. Trained hospital personnel typically read and diagnose EKGs, though technology exists for automated detection of some problems.

Mechanical cardiac tests include wall-motion assessment using echocardiography (i.e., diagnostic ultrasound) or MRI or CT. Contractility, and therefore overall motion, of the heart wall changes significantly during acute and chronic ischemia.

These changes can be visualized (and localized) using any of these imaging modalities. Exercise-induced ischemia can be visualized by performing these tests both before and after exercise. Functional assessment can also be done with these imaging modalities by calculating ejection fraction and other functional parameters from the acquired images.

Such conventional tests of heart function have several shortcomings. Continuous ambulatory monitoring with these devices is not practical. Although ambulatory EKG monitors (known as Holter or event monitors) can be used, they are typically not well tolerated for more than 24 hours at a time. Electrical abnormalities are not apparent in a large number of patients suffering from acute coronary events, including a significant population of patients with so-called non-ST-elevated MI. Also, these monitors require some expert diagnosis, reducing their desirability outside of the hospital. Finally, the external nature of these diagnostic tools reduces their sensitivity and ability to localize events to a specific region within the heart.

In an attempt to address these issues, technologies have been proposed for implantable ischemia detection through electrodes placed within the ventricle or chest cavity, to monitor electrograms within the heart. These devices may use an automated processing algorithm for determining whether ischemia is present based on the recorded electrograms, and are typically placed along an electrical lead placed in the atria or ventricles. Other proposed implantable devices measure biochemical markers for ischemia. Chemical sensors for this purpose are sometimes deployed in coronary arteries for local ischemia detection. Upon detection of an event, these implantable devices can alert the patient of danger or deliver early therapy.

However, these technologies have significant shortcomings in the early diagnosis of myocardial ischemia and other cardiac dysfunction. In particular, techniques are used that have a low sensitivity to early ischemic events. In the case of electrogram recording, there is a reliance on measurements that can return to baseline rapidly after reperfusion, making diagnosis of transient events or stunned myocardium difficult. In addition, electrical signals are susceptible to interference from other implanted devices, including electrical pacing and defibrillation pulses. Certain biochemical analyses (such as CK-MB) measure events that occur hours after the onset of ischemia.

Coronary heart disease (CHD) is the leading cause of death in the United States for both men and women. The importance of this disease, and the significant deficiencies in current diagnostic methods, make improvement in detection highly desirable. The present invention addresses these issues.

PUBLICATIONS

U.S. Pat. No. 6,514,195 describes an implantable device that analyzes blood flow rate. U.S. Pat. No. 6,501,983 describes an implantable system comprising a plurality of devices. EKG-based implantable devices, for example to detect ST segment shift, are described in International Patent Application Publication Nos. WO03/020366; and WO03/020367; and in U.S. Pat. No. 6,609,023. An implantable accelerometer is described, inter alia, in International Patent Application Publication No. WO98/14239.

BRIEF SUMMARY OF THE INVENTION

Devices and methods are provided for monitoring of heart function through determination of the total motion of the heart. In certain embodiments, the total motion of the heart is determined by the motion of the heart at its apex. The direction of apical movement provides a sensitive, immediate and accurate indicator for cardiac dysfunction, particularly ventricular dysfunction, because there is a change in the vector of movement at the apex when there is a lack of proper contraction. Such mechanical changes in heart function are more pronounced than electrical dysfunction, and persist even after reperfusion. Further, mechanical signals utilized in the present invention are not subject to interference from electrical pacing signals generated by implantable pacemakers.

Devices according to the present invention are intracorporeal, usually implanted, and may be used for continuous, automatic monitoring, thereby providing early diagnosis of acute myocardial ischemia or infarction. The early diagnosis allows for immediate therapeutic intervention, e.g., hospitalization, pharmacologic intervention, and the like.

The present invention includes the use of monitoring devices (sensor) placed at one or more cardiac location, often at the apex of the left or right ventricle, but the sensor(s) may be placed elsewhere on or in the heart. In one embodiment, there is a single measurement sensor, which may comprise a lead to operably link elements of the device, or may be free of leads. In an alternative embodiment, multiple measurement sensors are provided, e.g., for pacemaking, monitoring EKG, blood chemistry, and the like. Additional sensors may be mechanical, electrical, hemodynamic, chemical, etc., sensors. Sensor output during a period of normal function is analyzed by a programmable device, which is used to determine the boundaries of normal movement. Optionally, a transiently induced abnormality, e.g., occlusion, is performed to determine the alteration in apical movement during a lack of proper contraction. Thresholds are set for normal performance, such that movement outside of the normal thresholds activates a warning or other therapeutic action.

In one embodiment of the invention, the monitoring device is permanently or semi-permanently implanted in the body. The device is optionally integrated into a pacemaker, or other implantable device, or alternatively is implanted as a stand-alone sensor. Particularly for a stand-alone device, the delivery of said sensors into the heart may be percutaneous or transthoracic.

In some embodiments, a system for detecting cardiac dysfunction is provided. The minimal elements of the system include a sensor at the ventricular apex, which may be positioned at the left ventricle or the right ventricle; and a motion analysis (MA) element. The MA element may be implanted, e.g., integrated into a pacemaker with leads to the sensor, integrated into the sensor; provided as a stand alone unit with leads; subcutaneously implanted, etc.; or may be external, e.g., reversibly attached to the skin; as a handheld device, etc. The sensor and the MA element are operably linked, through electrical leads, radiotelemetry, integrated circuitry, etc. The sensor provides a monitoring of movement at the ventricular apex, and the MA element analyzes the movement output to determine if the direction and/or distance of movement falls outside of a pre-set threshold, thereby indicating a dysfunction.

The system will usually further comprise a programmable device (programmer), which analyzes the output of the apical movement sensor. Typically the programmable device will include software for analysis of normal function, and will be used to input data. The programmer can provide the patient's doctor with the capability to set cardiac event detection parameters, or threshold levels. The programmer communicates with the MA element, e.g., through a USB port, wireless communication, etc., and may share a communication system with an alarm element. The programmer can also be used to upload and review data captured by the MA element, including data captured before, during and after a cardiac event. The programmer may further record and store data from a patient, e.g., to follow cardiac function over a period of time, to assess changes in performance during the lifetime of a patient, in response to therapeutic regimens, and the like. The programmable device may be available at a hospital or physician's office, or may be a personal computer, PDA, etc., although threshold analysis and modification is preferably performed under control a health professional. It may also be desirable to choose the predetermined time in the past for comparison to take into account daily cycles in the patient's heart movement signals. Such a system would adapt to minor slow changes in the patient's baseline movement, as well as any daily cycle changes.

The system may further comprise additional implantable sensor or sensors, for example sensors that are capable of analyzing mechanical, electrical, chemical signals, etc. Such additional sensors may be operably combined with the apical motion sensor.

Using one or more detection algorithms, the MA element can detect a change in the patient's ventricular apical movement that is indicative of a cardiac event, such as an acute myocardial infarction, within five minutes after it occurs and then automatically warn the patient that the event is occurring. To provide this warning, the system may further comprise an internal or external alarm element, which is optionally integrated into the MA element. The alarm signal may be a mechanical vibration, a sound; a transmission to a medical facility; and the like. The alarm element may further comprise an "alarm-off" button that when depressed can acknowledge that the patient is aware of the alarm and will turn off internal and external alarm signals; and a display (typically an LCD panel) to provide information and/or instructions to the patient by a text message and the display of the motion sensor.

In the methods of the invention, cardiac function is assessed by monitoring the total motion of the heart, and particularly the motion of the apex of the heart, with at least one motion sensor implanted at, on or in the heart. The cardiac or apical motion may be sensed in one or more directional axes, such as the anterior-posterior direction relative to the heart. The sensed signals are processed to provide an output as a result of the processing. Other sensors may also be used for measuring or monitoring other cardiac parameters, such as for example, an electrocardiogram. The methods may also involve filtering out certain signals, such as signals having a frequencies above about 10 Hz in order to eliminate signals that are not necessarily indicative of directional movement, but of a character of the movement such amplitude of the signal. Processing the sensed signals processing comprises relating the signals to at least one predetermined baseline value of the movement of the apex of the heart. Any baseline value may be used, such as parameters representative of the patient's normal apical movement. The output may be a signal or event, such as a cardiac pacing signal, the delivery a therapeutic agent to the heart or an alarm signal in the event where a processed signal is determined to be outside a predetermined threshold range. In certain embodiments, the output may be an indication of an ischemic condition of the heart, such as a location of an ischemic area, a location of an occluded coronary artery or the degree of the ischemic condition.

These and other features, objects and advantages of the invention will become apparent to those persons skilled in the art upon reading the details of the invention as more fully described below.

BRIEF DESCRIPTION OF THE DRAWINGS

FIG. 4 illustrates four preferred embodiments of the device as placed in the heart in cross-sectional view, located either (a) in the proximal anterior interventricular vein, (b) in a plurality of locations spanning the ventricle, (c) in the ventricular apex and atrial appendage, or (d) in the ventricular apex and coronary sinus.

FIG. 7 illustrates four potential configurations of sensors within a leadless device, with either (a) a plurality of noncoaxial sensors within a localized implant, (b) a single sensor within a localized implant, (c) a plurality of localized sensors at locations within an extended implant, or (d) an extended sensor within an extended implant.

DETAILED DESCRIPTION OF THE EMBODIMENTS

Figure 1:
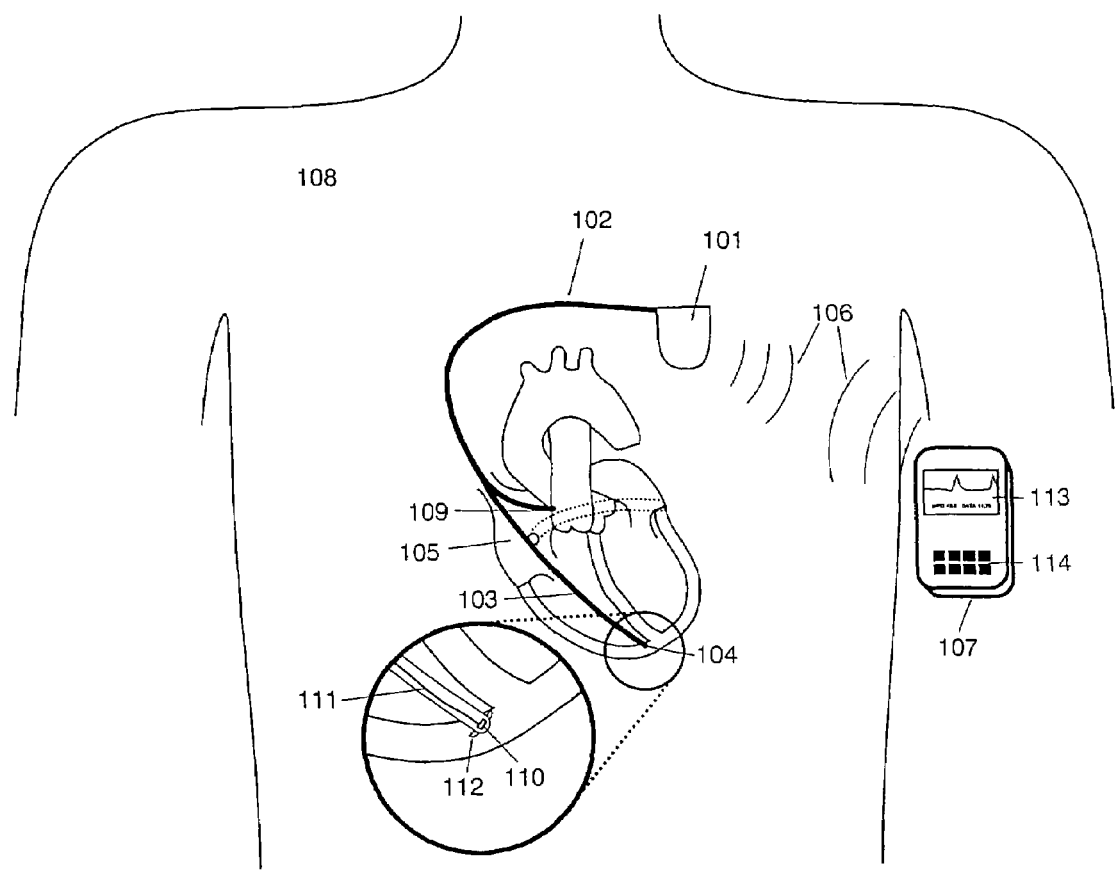
FIG. 1 is a cross-sectional view of the chest and heart including an implantable device with a sensing lead and means for communication with an external device.

Devices and methods are provided for monitoring of heart function, which devices comprise a sensor for the determination of the motion of the heart at the ventricular apex, particularly the direction of motion. The direction of apical movement provides a sensitive, immediate and accurate indicator for cardiac dysfunction. Specifically, the 6-degree-of-freedom path that the ventricular apex traverses over time changes abruptly and significantly under acute ischemia, and the characteristics of that change can be assessed in order to deduce that an ischemic event has occurred, and which coronary artery was likely to be responsible for the ischemia. Apical motion can also be analyzed to assess heart rate, detect the presence of arrhythmias, detect pacing signal capture, volume overload, or other signs of heart dysfunction. The information contained in the motion of the apex can be combined with information from one or more EKG electrodes or pressure transducers (or any of the other previously defined sensor types) in order to gain further sensitivity and specificity to heart dysfunction including myocardial stunning, hibernation, infarction, and ischemia.

In accordance with one embodiment of the invention, there is disclosed an implanted, or intracorporeal device for detection and monitoring of cardiac dysfunction comprising: means for motion sensing at the apex of the heart; a motion analysis element providing a means for interpreting signals generated by the sensor; and means for indication of dysfunctional state as a result of said analysis, e.g., alarm, remote site transmission, etc.

Such a device provides a method for detection and monitoring of cardiac dysfunction comprising the steps of: sensing one or more properties of cardiac tissue or blood; interpreting signals generated by said sensing elements; which signals are an indication of a dysfunctional state as a result of said analysis. The device may be manufactured in a variety of configurations, including a sensor operably connected to an MA element, where the MA element is implanted or external; a sensor operably linked to an implantable device, such as a pacemaker; cardioverter; defibrillator; infusion pump; annuloplasty ring; atrial appendage occlusion device, or other implantable cardiac therapy; the method comprising the steps of: integration of circuitry for sensing one or more properties of cardiac tissue or blood, interpretation of signals generated by said sending elements, and indication of dysfunctional state as a result of said interpretation.

An intraluminal catheter for the delivery of a cardiac-monitoring sensor is also provided, which catheter may comprise an elongated shaft having proximal and distal ends, at least one detachable portion of the catheter located at the distal end, a detachment mechanism allowing the release of the detachable portion from the shaft, and an actuator located at the proximal end for actuation of said detachment mechanism.

In accordance with this embodiment of the invention, methods are provided for detection and monitoring of cardiac dysfunction comprising: sensing the path that the cardiac ventricular apex traverses over time, interpretirig signals-generated by said sensors; and producing a physiologic or environmental effect or output as a result of said analysis. The method may include the steps of implanting at least one sensor; interrogating of the sensor(s), e.g., using a remote device; and analysing of at least one physiological variable as sensed by the sensor.

Ischemia. One application of the present invention is the sensing and analysis of ischemia to the heart. As discussed above, EKGs are often used to determine the extent of ischemia caused by an ischemic event. It has been observed that acute ischemia results in mechanical changes to the heart which are more pronounced than electrical changes to the heart, and that this mechanical dysfunction (e.g., a decrease in local "shortening" of the ischemic area) may persist longer than electrical dysfunction, even after reperfusion has occurred. See *J Invasive Cardiol* 1999; 11:329-336. In particular, we have observed that the axis of apical motion can vary from the baseline axis by as much as between about 30° to about 45° (see FIG. 13). Additionally, the particular direction(s) in which the axis of apical motion has changed can be correlated to a specific location of ischemia, e.g., an arterial occlusion. As such, one or more sensors positioned at the apex of the heart for sensing the apical motion of the heart may be highly beneficial in assessing the ischemic conditions of the heart (e.g., location of an arterial occlusion, extent of ischemic damage, etc.).

In one embodiment of the present invention, one or more apical motion sensor, such as an accelerometer, is positioned at the apex of the heart, e.g., in the right ventricle, to sense the motion, i.e., the acceleration, of the mass of the heart as a whole. In certain variations of this embodiment, the sensor is adapted to be particularly sensitive to low-frequency motion in order to distinguish between signals representative of bulk motion of the heart relative to its surroundings (i.e., having fundamental frequency of around 1 Hz and all significant harmonic frequencies less than about 10 Hz) and those accelerations arising from vibratory or non-cardiac motions of the heart (e.g., the vibratory motion arising from the pressure wave associated with the closing of the mitral valve) which are typically in the range from about 5 Hz to about 100 Hz as taught in PCT Patent Application Publication No. WO 03/020366. In still other variations, the sensor may be adapted to filter out these higher frequency signals so as to eliminate any skewing of the desired measurement that the high frequency signals may cause. One example of a suitable motion sensor for use in the context of the present invention is the Analog Devices ADXL330, a microchip MEMS-based 3-axis accelerometer that is sensitive to accelerations up to approximately ±2 g. This device can be configured for sensitivity to low frequencies by appropriate adjustment of its bandwidth, e.g., within the range of 5-10 Hz. This choice of bandwidth removes unwanted high-frequency motion and simultaneously improves sensitivity to motions in the desired range.

Further, the subject motion sensors may be adapted to be particularly sensitive to acceleration in axes perpendicular to the sensor's lead. Because abnormalities in cardiac function manifest themselves as changes in acceleration perpendicular to the long axis of the heart (and therefore the lead), such a lead configuration may enhance the sensitivity of the device to such abnormalities. The sensor may be configured to sense motion in a single axis (e.g., the anterior-posterior ('Y') axis) or a multiple-dimensional sensor to provide two or three-dimensional measurements. Rotational motion sensors may be used instead or in addition to position sensors; using both position and rotation sensors, up to six degrees of motion information can be gathered for assessment of the ischemic condition. The greater the number of dimensions or degrees of apical motion assessed, the more precise the acceleration measurement and the more information that can be determined (e.g., precise location of arterial occlusion, extent of ischemic area, etc.) from such measurement, and the greater the ability to assess other cardiac conditions (e.g., CHF, arrhythmias, etc.).

If a multidimensional accelerometer sensitive to gravitational acceleration (e.g., the Analog Devices ADXL330) is employed, then the change in direction of the gravity vector relative to the sensor, over the cardiac cycle, can be monitored instead of or in addition to the dynamic cardiac acceleration to provide diagnostic or ancillary information. For example, the orientation of the gravity vector may be used to determine whether the individual is upright, laying down, or otherwise, and may be configured to only perform monitoring in one or more body orientations or to recalibrate the detection algorithm based on body orientation. Knowledge of the gravity vector may also be used to distinguish periodic heart motion from other body motions (e.g., jogging), thereby obviating the need to use another sensor as a reference sensor. Moreover, the periodic variation in the detected gravity vector may itself be used to diagnose the ischemic state, because changes in the axis of apical motion would manifest themselves as changes in the periodic excursion of the gravity vector for any given body orientation.

In the chronic disease known as congestive heart failure, the heart's pumping ability decreases. This is followed by ventricular remodeling, in which the ventricle changes shape (usually by enlarging) to compensate for the decrease in pumping ability. An apical motion sensor may detect portions of this process. For example, any decrease in the mechanical vigor of any portion of the ventricle will result in a decrease in the amplitude of motion of an apical motion sensor. The absolute location of the sensor with respect to a fixed reference may also change measurably over time as a result of ventricular remodeling. These changes can be differentiated from ischemic events both by their slow onset (requiring hours to days to occur) in addition to the fact that the axis of motion is relatively unaffected. If multiple motion sensors in the ventricle are used, then contractility may be measured by analyzing sensor motion with respect to one another. Current methods for intracardiac monitoring of pumping ability focus on pressure measurement, which is difficult to achieve reliably in the left side of the heart (as is desired), and cannot provide the range of diagnostic information that is available with motion sensing. If desired, motion sensors may be used in conjunction with pressure sensing for enhanced diagnostic accuracy.

Two common arrhythmias in those with heart disease are ventricular tachycardia and ventricular fibrillation. In ventricular tachycardia (premature ventricular contractions), the ventricle contracts rapidly and out of rhythm with atrial conduction. In ventricular fibrillation, the ventricle twitches rapidly, but no coordinated contraction occurs. Therapy for ventricular fibrillation (defibrillation shocks) must be administered rapidly in order to restore blood flow to the body. In contrast, ventricular tachycardia may be treated less aggressively because blood is still flowing to the body. Current implantable defibrillators use EKG sensors to detect and discriminate ventricular tachycardia from ventricular fibrillation, but the electrical waveforms for these two distinct conditions may be too similar for accurate automated discrimination.

A mechanical sensor at the apex of the heart could improve the accuracy of discrimination between ventricular tachycardia and ventricular fibrillation because any concerted contraction would result in significant apical motion, while uncoordinated twitching (as in ventricular fibrillation) would not result in significant apical motion. Ventricular tachycardia and fibrillation may also be detected using only an apical motion sensor by analyzing the periodic rate and amplitude of sensor motion. Ventricular tachycardia is characterized by contraction rates of 160 to 240 beats per minute, while ventricular fibrillation has a less consistent rate and lower amplitude of sensor motion.

When a pacemaker is implanted, the strength of electrical shock is carefully set so that it is strong enough to be 'captured' and cause a ventricular contraction but not so strong as to cause myocardial damage or to unnecessarily use battery power. This may be difficult with electrical sensing (as is commonly used) because the electrical pacing pulses interfere with electrogram recordings, making determination of pacemaker capture difficult. A mechanical sensor at the apex improves capture detection because it is not susceptible to this type of electrical interference, and can be used to detect cardiac contraction.

As such, in one variation of the invention, one or more mechanical sensors are used to sense the overall motion of the heart relative to its position within the chest cavity, perhaps in conjunction with one or more electrical sensors. An MA is employed to analyze the sensed signals for its motion amplitude synchronized with the pacing pulses, with any motion above a determined baseline level categorized as a captured heartbeat. This MA may also be configured to use the signal (s) sensed from the one or more mechanical sensors as a reference signal to further analyze and/or interpret the electrical signals sensed by the electrical sensors. In this way, the mechanical sensor(s) is used to minimize the potential error due to the interference of electrical pacing pulses or other electrical pulses.

Heart Dysfunction. As used herein, heart dysfunction or disease state refers to myocardial ischemia, necrosis, low ejection fraction, reduced cardiac output, dilatation, volume overload, heart failure, cardiomyopathy, acute coronary syndromes including unstable angina and acute myocardial infarction, stable angina, cardiac arrest, tamponade, pericarditis, arrhythmias including ventricular tachycardia, ventricular fibrillation, bradycardia, supraventricular tachycardias, atrial fibrillation, pacing signal capture, and other physically or electrically manifested cardiac states.

Apex. As used herein, the term "apex" of the heart refers generally to the location 501, shown in FIG. 5. This location may include, without limitation, endocardially at the right-ventricular apex, at the epicardial apex, in an apical cardiac vein such as the anterior interventricular vein (AIV); etc. Information about apex motion might also be inferred from nearby locations such as the esophagus or airway. The apical location of a sensor is desirable because mechanical dysfunction anywhere in the ventricle causes absolute changes in motion of the apex.

Sensor. Sensors are used in the present invention to detect physiological variables relevant to heart function. The sensor is operably linked to a motion analysis element, where the operable linkage may be wired or wireless. At least one sensor provides a monitoring of movement at the ventricular apex.

The measurement sensor is preferably used as a long-term implant, but may also be used temporarily or transiently; e.g., during a catheterization procedure or during a patient's hospital stay. Implantation may be performed during a catheterization procedure; at the time of thoracic surgery; through a minimally invasive procedure accessing the pericardial space; and the like.

One or more motion sensors may be placed in locations in proximity to the ventricle wall. These locations may be accessed using the cardiac veins, placed epicardially, located in the esophagus, or placed inside the ventricles themselves. Motion measurements are used for accurate assessment of the location of the origin of the dysfunction, as well as providing increased sensitivity and specificity to acute events and other dysfunction. For example, in the case of ischemia, the ischemic region can be localized by analyzing the direction of acute change in the motion of the ventricle wall. Referring to FIG. 5, if an apical sensor is present at location 501, then ischemia results in an abrupt change in the motion of the apex that tends to be directed away from the location of the ischemic region (compare motion paths 504 and 506).

The term 'measurement sensor' or 'sensor' may refer to an RF telemetry device, a gyroscopic element, piezoelectric element, ultrasonic transducer (using either transmission or reflection signals), contractility sensor, capacitive sensor, conductance sensor, strain gage, angular rate gyro, or accelerometer. Here, the term RF or radiofrequency refers to any form of electromagnetic energy, but is preferably within the range of 1 kHz-1 GHz. However, with respect to those sensors employed as motion sensors, and particularly those employed at the apex of the heart to measure the overall motion of the heart relative to the chest cavity, very low frequency sensors are needed. The contractibility of the human heart is typically in the range from as low as about 20 beats per minute in a patient suffering from severe bradycardia, to between about 50 to about 100 beats per minute for a normally functioning heart at rest, to between about 100 to about 200 beats per minute in a normal heart during exercise, to as much as about 240 beats per minute with a heart in severe tachycardia These rates translate into apical motion frequencies in the range from less than about 0.3 Hz to about 4 Hz or more. Because the motion is not purely sinusoidal, additional periodic modes will also be present at harmonic multiples of this fundamental frequency; e.g., if the pulse rate is 60 bpm, then the fundamental frequency present will be at 1 Hz, but harmonic information will be present at 2 Hz, 3 Hz, 4 Hz, and so on. Typically, the amount of energy present in each harmonic decreases as its frequency increases; in this case, we can assume that the periodic motion is well characterized by its fundamental frequency and two or three harmonic frequencies. As such, in certain embodiments, the apical motion sensors are adapted to sense frequencies in the range from less than about 0.3 Hz to about 10 Hz. When used with other sensors, this measurement ensures accurate interpretation of other sensed signals representative of the heart's motion. When used alone, such an apical motion sensor filters out or just does not detect higher frequency signals produced by the heart.

Other measurement sensor types may be microphones, flow meters, pressure transducers, electrodes, conductivity sensors, compliance sensors, capacitive sensors, or biochemical sensors using concentration sensors, light-scattering or reflectance or Raman spectroscopy, interferometry, or biologically reactive microsensors. Any or all of these measurement sensor types and measured parameters may be used alone or in combination in order to provide diagnostic information about the heart's disease state.

While the invention provides for detection of the apical heart motion, including position, velocity, acceleration, rotation, or rotation rate, other properties may also be sensed. In one embodiment of the invention, additional sensors are implanted, which provide measurement of properties including heart sounds, contractility, blood flow, electrical conductivity, electrogram signals, tissue compliance, fluid pressure, wall strain, or concentrations of electrolytes, ions, or biochemical markers in the blood or tissue. For example, while only a single accelerometer sensor may be employed to assess a heart's ischemic conditions (as discussed above), EKG sensors (or other sensors) maybe employed to provide further data (e.g., ST elevation) to enhance accuracy or to assess other cardiac parameters.

In one embodiment of the invention, the motion sensor is an accelerometer. Accelerometers can be designed to measure rotational or translational acceleration, as well as Coriolis acceleration in a vibratory rate gyroscope. Various accelerometers, including those comprising MEMS (MicroElectroMechanicalSystem), are commercially available and known in the art. For example, see U.S. Pat. Nos. 6,666,092; 6,671,648; 6,581,465; 6,507,187; 5,345,824; etc. Sensing using accelerometers can be accomplished, for example, by placing a reference accelerometer in a device casing external to the heart 101, and one or more measurement accelerometers at locations in or on the heart, for example at location 501. In other embodiments, the reference sensor is not present, and the motion of the patient is filtered; measurements are taken when stationary; or an external device, e.g., a programmer; MA element; etc. provides a point of reference.

For example, an accelerometer may be a surface-micromachined polysilicon structure, where deflection of the structure due to acceleration is measured by variations in capacitance between a suspended polysilicon mass and fixed micromachined plates. For this application, a commercially available device such as Analog Devices' ADXL330 MEMS three-axis accelerometer may be used, or a specialized device may be fabricated. For example, the MEMS may be equipped with signal conditioning, voltage reference, amplification, and demodulation functions integrated onto the accelerometer chip. Another advantage of MEMS is that they have a relatively small footprint (less than about 16 mm$^2$) and, thus, are easier to implant through minimally invasive means.

Measurement accelerometers indirectly measure local heart wall motion, while the reference accelerometer is used to remove effects generated by patient motion, respiration, and the like. Comparisons between signals generated by adjacent measurement accelerometers (if multiple measurement accelerometers are present) provide information about tissue contractility between those locations, and abrupt changes in such measures are good indications of acute events such as acute myocardial infarction or arrhythmia. Chamber blood volume can be calculated using the locations of a number of sensors around the entire ventricle, and meaningful parameters such as cardiac output and ejection fraction can be calculated using temporal variations in chamber volume.

Instead of accelerometers, a MEMS rate gyro, such as Analog Devices' ADXRS150 may be used for sensing of the angular rate of rotation of the heart at the location of the implant. Ventricular twist decreases markedly under acute ischemia, which can be used as a reliable warning of acute myocardial infarction. Other measures of cardiac dysfunction including ventricular tachycardia, ventricular fibrillation, supraventricular tachycardias, and parameters of congestive heart failure may also be made from these signals.

To differentiate heart motion from patient motion or respiratory motion, differential measurements are preferably made. This may be realized by placing one or more reference sensors located elsewhere in the body from the previously described measurement sensors, where reference sensors are preferably of the same sensor type as the measurement sensor. Measurement and reference sensors may be connected to each other and to processing circuitry via one or more leads, or may communicate via RF, acoustic or other telemetry in a leadless configuration. If a leadless configuration is used, a delivery device or catheter is typically used for percutaneous or transthoracic placement of the device into the appropriate anatomical structure.

Differential measurements may also be accomplished through an extended sensor, where physiologic conditions vary along the length of the sensor and an electrical or mechanical effect is achieved because of that variation. If a lead is present, tip motion including deflection or torsion may be detected relative to the rest of the lead. One or more reference sensors may also be used, and the data acquired from the reference sensor(s) can be used to correct for non-cardiac motion. If multiple measurement sensors are present, individual measurement sensors can be used to provide a reference for other measurement sensors. Reference sensors are preferably located in a basal location such as the atrial wall, atrial appendage, or coronary sinus, or they may be located subcutaneously, in the inferior vena cava, in the lead body, included in the implantable canister containing the device electronics, or anywhere in or on the body where interfering signals also occur.

In particular, differential measurements may be made using multiple leads placed in the cardiac veins. Current bi-ventricular pacemaker technologies locate two or more leads in cardiac veins, in locations approaching the cardiac apex. These leads may be particularly adapted for motion measurement, and a suitable algorithm applied to derive approximate apical motion from information gathered by these multiple non-apical sensors. Because multiple sensors are used, interfering motions may be automatically rejected by using this technique differentially.

If differential measurements are not made, noncardiac motion can be rejected through filtering, baseline subtraction, or other processing techniques applied to the data acquired from the measurement sensor(s).

Motion Analysis Element. The MA element in general comprises a data processing unit, usually a memory unit, means for receiving input data, and means for transmitting output. In one embodiment of the invention, the MA element is a canister-type unit in a pacemaker, in which the functions required for the present invention have been integrated. In another embodiment, the MA element is an implanted device specific for the present invention. In yet another embodiment, the MA element is an external device, operably linked by a wireless connection, which may be removably attached to the patient; or may monitor input from a remote location, e.g., a data hub; integrated with a PDA or personal computer, and the like.

Figure 11:
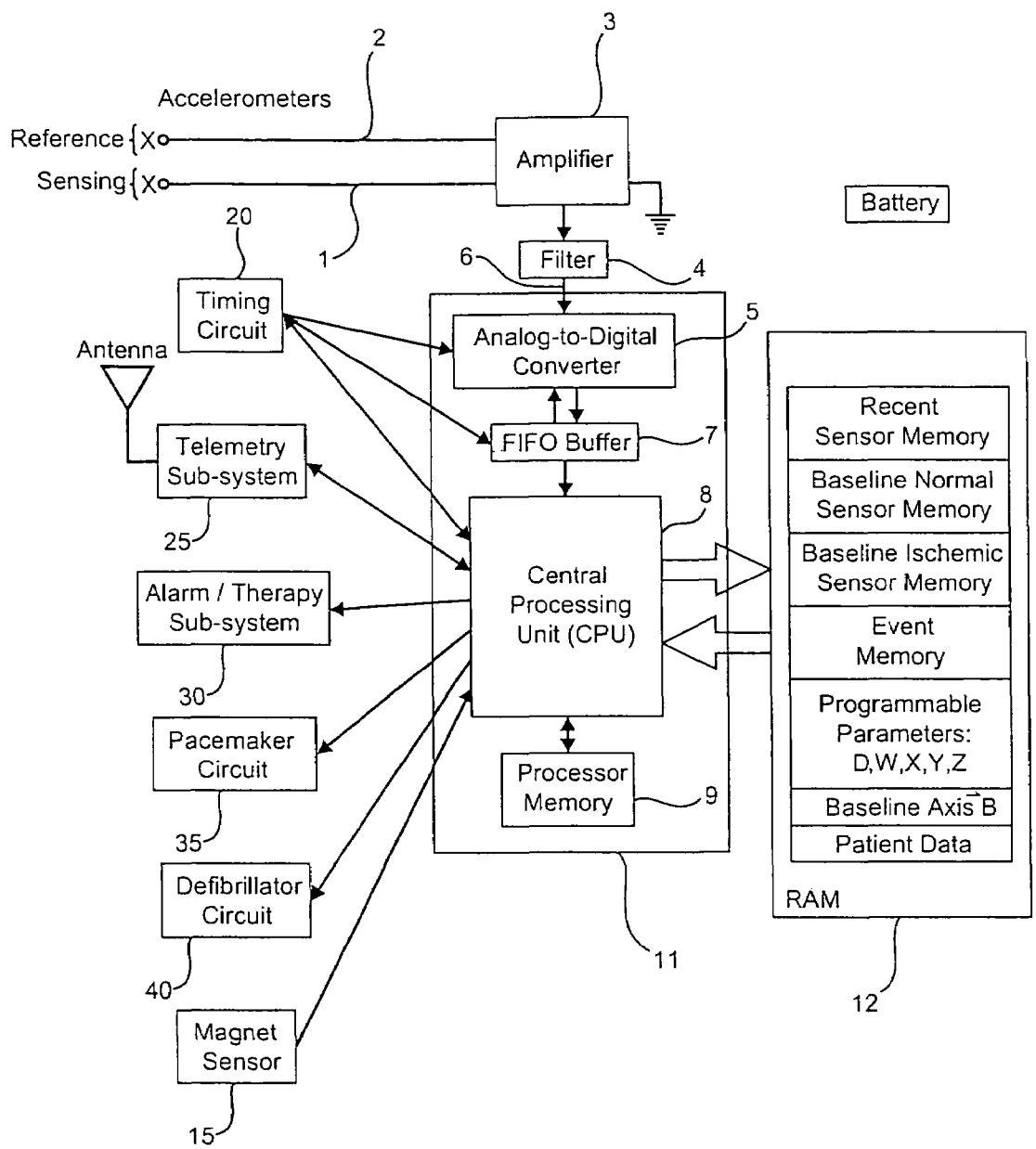
FIG. 11 provides a schematic for a motion analysis element.

A schematic of sensors operably linked to an exemplary MA element is shown in FIG. 11. The MA element provides a means of processing signals from a measurement sensor 1 and a reference sensor 2. The signal is amplified by an amplifier 3 and run through a filter 4, and an analog to digital converter (ADC) 5. Usually, although it is not required, the filter 4 is included in the sensor; and the ADC 5 is included in the MA element.

There is an operable connection 6, between the sensor elements and the MA element. The operable connection may be an electrical lead, an integrated circuit, a radio frequency transmission; and the like. The MA element 10 comprises a FIFO buffer 8, a central processing unit (CPU) 9, and a processor memory 11. The CPU is provided with a variety of information, usually in RAM 12, which may include recent sensor memory, baseline normal sensor memory, baseline ischemic sensor memory, event memory, programmable parameters, including thresholds for dysfunctional performance, baseline axis, patient data, and the like.

In addition to the motion sensors, the MA element may receive data input from additional sensors, e.g., a magnet sensor 15; timing circuit 20; telemetry sub-system 25. The MA element may transmit instructions, data, etc. through the telemetry sub-system 25; and may control, for examples, an alarm/therapy sub-system 30; a pacemaker circuit 35; defibrillator circuit 40, timing circuit 20; etc.

Thresholds. The MA element is usually programmed with thresholds for movement parameters, and optionally for other parameters where such sensors are present. Motion that varies from the normal motion by a preset amount will trigger the alarm or other warning system.

Figure 10:
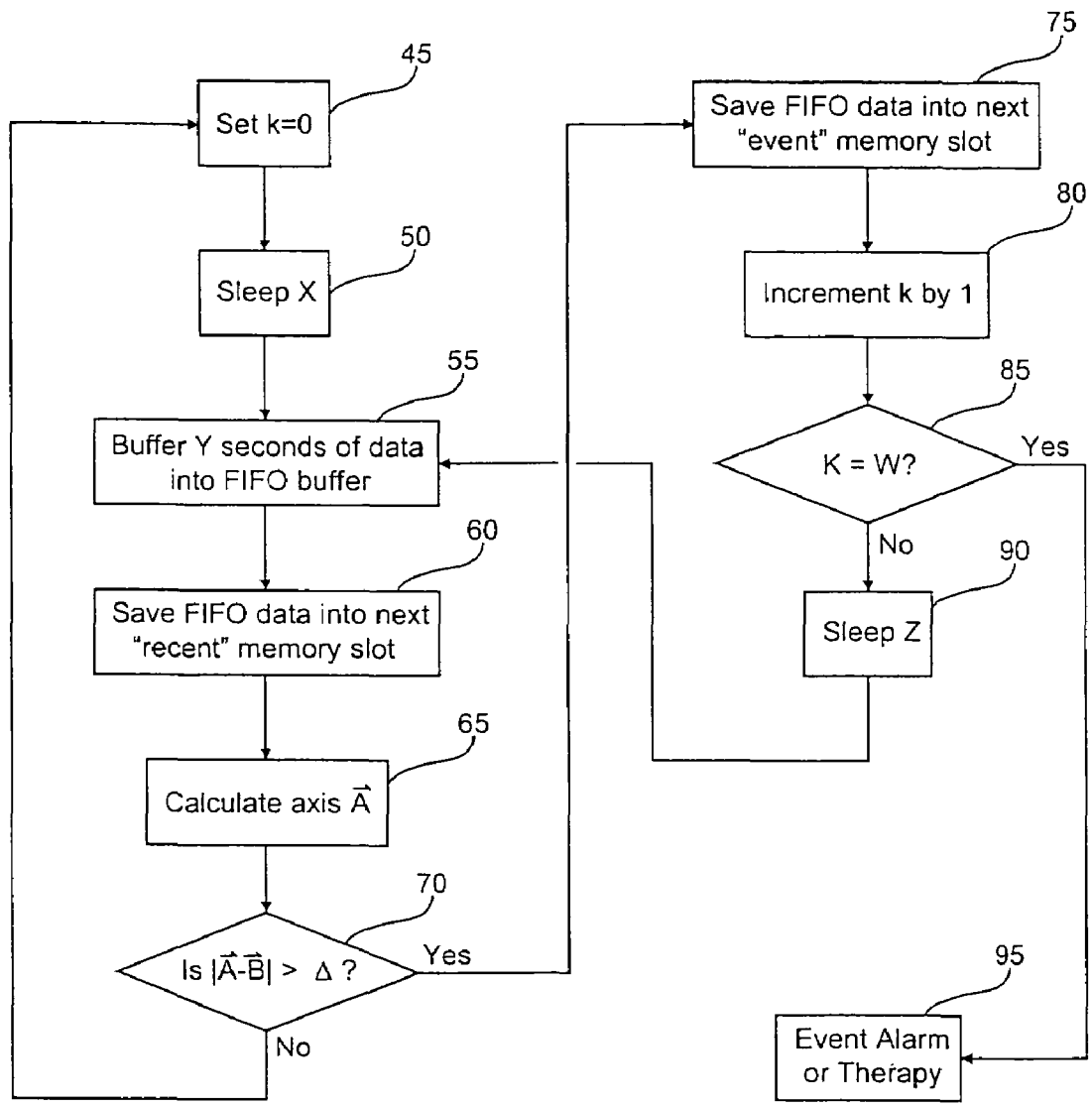
FIG. 10 provides a flow chart for data analysis in the methods of the invention.

The flow chart in FIG. 10 depicts the data analysis algorithm. The sleep X 50 is the time between ischemia checks under normal conditions. A buffer 55 of Y second of data is input into the FIFO buffer, where Y is the amount of data recorded for one ischemia checking iteration. The FIFO data is saved into the next recent memory slot 60, and 65 the axis A is calculated, where A is a unit vector representing the current axis of motion of the apex. The vector A is compared to a vector B, where B is a unit vector representing the 'baseline normal' axis of motion of the heart, as determined from data collected either during a physician visit or at some previous time point determined to be normal. The comparison 70 is evaluated relative to Δ: the maximum allowable deviation in the axis of motion (threshold) from the baseline normal value as determined from the accelerometer sensor data. This parameter can range from about 0 to not more than about 1.414 ($\sqrt{2}$), and is preferably from about 0.1 to about 0.4, and more preferably from about 0.15 to about 0.3, which provides a deviation of about 10-20% deviation from normal before an alarm sounds.

Where the difference between A and B is less than Δ, the algorithm loops back to 45. Where the difference between A and B is greater than Δ, the FIFO data is saved into the next event memory slot 75, and 80, the counter variable K is incremented by 1. K is a counter variable used to keep track of how many consecutive positive ischemia checks have occurred. If it's bigger than W, then an alarm is triggered. K is compared to a present parameter W 85, where W is the number of consecutive positive ischemia checks required before an alarm sounds. If K=W, then the event alarm or therapy 95 is activated. If K is less than W, then sleep Z is activated 90, where Z is the time between ischemia checks when an ongoing event is suspected.

Programmable device (programmer). Implementation of the present invention will preferably utilize a programmable device, which analyzes the output of the MA element. Typically the programmable device will include software for analysis of normal function, and will be used to input data and set initial thresholds for Δ, X, W, Z, and to record the initial baseline vector B. The programmer can provide the patient's doctor with the capability to set cardiac event detection parameters, or threshold levels. The programmer communicates with the MA element, e.g., through a USB port, wireless communication, etc., and may share a communication system with an alarm element. The programmer can also be used to upload and review data captured by the MA element, including data captured before, during and after a cardiac event. The programmer may further record and store data from a patient, e.g., to follow cardiac function over a period of time, to assess changes in performance during the lifetime of a patient, in response to therapeutic regimens, and the like. The programmable device may be available at a hospital or physician's office, or may be a personal computer, PDA, etc., although threshold analysis is preferably performed under control a health professional. It may also be desirable to choose the predetermined time in the past for comparison to take into account daily cycles in the patient's heart movement signals. Such a system would adapt to minor slow changes in the patient's baseline movement, as well as any daily cycle changes.

Alarm/therapy sub-system. Indication of heart dysfunction is preferably accomplished with an audible signal from the implanted device, but may also be accomplished via RF telemetry to an external device (which itself notifies the patient appropriately), electric shock, nerve stimulation, administration of drugs with a rapid perceptible effect, vibration, or telecommunication via cellular telephone, wireless LAN, or other network. Therapies, if administered, may include administration of drugs or dose modification of an ongoing drug regimen, including antiarrhythmic agents, diuretics, antiplatelet agents, inotropic agents, aspirin, and the like. Alternatively, therapy may be administered by devices using ultrasound energy, electromagnetic energy, or nerve stimulation for clot dissolution, cardioversion, cardiac pacing, ablation, fluid volume reduction, reduction of cardiac load, or other therapeutic effect. For therapeutic purposes, a drug reservoir and drug-delivery apparatus may be incorporated into the device, or other devices that produce therapeutic effects as are known in the art.

Pacing signal capture or myocardial capture refers to the condition when an electrically generated pacemaker stimulus produces a coordinated contraction of the heart; electrical pacing signals that are too weak may not provide such capture, while pacing with too much energy may cause damage and results in shorter battery life. Analysis and processing may consist of threshold analysis, waveform comparison, time-domain or frequency-domain analysis, multidimensional analysis of a number of waveforms simultaneously, analog-to-digital conversion, filtering, differential or integral analysis, linear or matrix analysis, or a combined approach.

One embodiment of the current invention provides for a short-term analysis of cardiac function. For example, it may be desirable to test the parameters of function described herein after a suspected ischemic event has occurred. Where a permanent implantation of the sensors is not desired, a catheter comprising one or more sensors may be utilized. For a catheter-based apical motion sensor, the catheter may be advanced to the right ventricular apex and forward pressure applied by the physician at the proximal end of the catheter to maintain contact between the distal tip of the catheter and the myocardium at the apex. The resulting motion of the catheter tip may be measured by the accelerometer or other sensor at the distal tip, and data collected and interpreted by an MA element located external to the patient. Alternatively, instead of applying forward pressure, the distal catheter tip could comprise an attachment mechanism that is actuated by the physician at the proximal end of the catheter to provide stable but reversible attachment of the device to the apical myocardium. One or more sensors can be placed along the length of the catheter to indicate local changes in one or more sensed physiological variables, which may be analyzed or processed to provide an indication of heart dysfunction to the patient or trained medical personnel. Therapy may also be delivered for immediate treatment of the detected dysfunction, or the device can indicate the need for specific therapy to the patient or health professional.

The sensed physiological property may be output by the device and analyzed by a physician, EMT, nurse, or other medical personnel to diagnose one or more heart dysfunctions. Alternatively or additionally, the device may analyze or process this signal to estimate the likelihood of an acute event or change in heart function. If the estimated likelihood is high, then the device could indicate this determination to the patient or to medical personnel.

The device itself may stand alone or be integrated into other implantable devices including pacemakers, implantable defibrillators, cardioverters, ventricular assist devices (VADs), event monitors (e.g., implantable EKG recorders or Holter monitors), infusion pumps, annuloplasty rings, atrial occlusion devices, or other surgical or catheter-deployed therapies. Power may be supplied to the device via electromagnetic telemetry, voltaic cells, batteries, acoustic telemetry, electrical conduction through tissue, or power generation from a physiologic or environmental energy source such as heat, light, flow, motion, contraction, or biochemical reactions.

One embodiment of the present invention is illustrated in FIG. 1, and includes an implanted canister 101 containing electronics for processing and storage of sensed data, as well as means for communicating the sensed information to the patient, medical personnel, or other parties. This embodiment of the device provides a lead 102 containing one or more sensors at locations including the end. This lead is advanced through the right ventricle 103 and affixed into the wall of the right ventricle near the apex 104. A sensor placed at the distal end of the lead 104 is thereby sensitive to abnormalities in the apical motion, conduction, torsion, contractility, or other property of the heart at this location. An additional sensor may be located in the portion of the lead traversing the right atrium 105 to serve as a reference sensor, or to increase the sensitivity of the device to atrial phenomena such as atrial fibrillation.

The magnified view of 104 shows an accelerometer sensor 110 (although any type of motion sensor may be used); a wire 111 connecting the accelerometer sensor with an MA element, in this case an implanted canister 101 comprising data processing means. Also included is a means 112 for anchoring a ventricular lead into the myocardium at the apex, which may also orient the sensor with respect to the apex.

Figure 12:
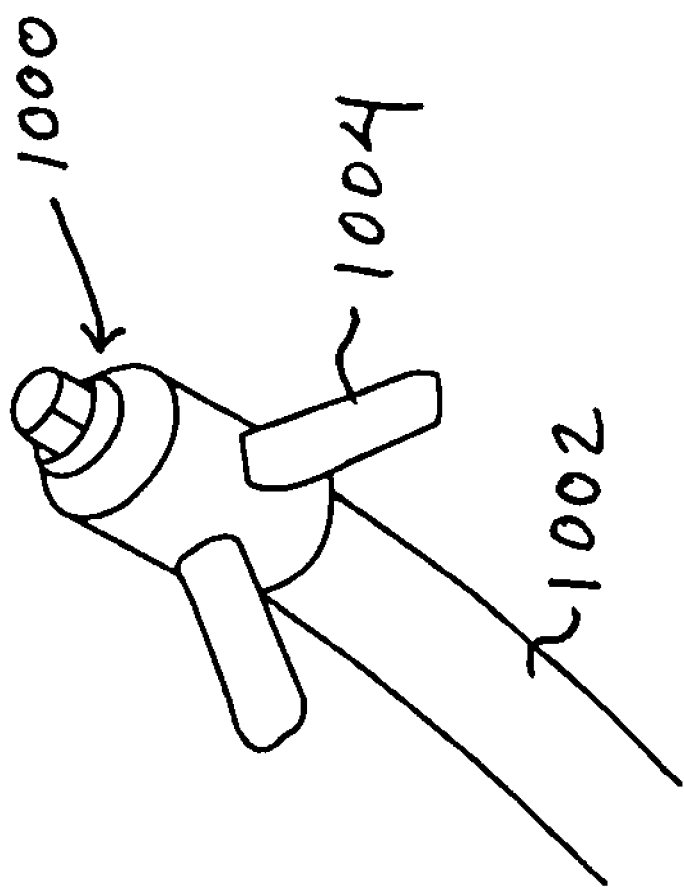
FIG. 12 illustrates an exemplary sensor lead of the present invention.

Another exemplary sensor lead structure for use with such applications of the present invention is illustrated in FIG. 12. A sensor 1000 is provided at the distal end of a lead 1002. Optional elements, barbs, prongs, etc. 1004 may be provided to facilitate anchoring of sensor 1000 within the implant site. In order to reduce the number of wires required in the lead body when a multidimensional sensor or multiple sensors are used, the signal may be multiplexed in time or frequency before transmission through the wire. If some sensor data is redundant in a known or measurable way, the sensor outputs may be linearly combined, using, e.g., a simple resistive network, to produce an output -representing the weighted sum of sensor signals. Means may be provided for adjusting the relative weightings of each signal, e.g., by adjusting resistances in the resistive network, at the time of implantation or afterward. This may be particularly useful in the case of a multidimensional sensor, which can be implanted in an arbitrary orientation and later adjusted so that its output represents motion along a specific axis relative to the patient known to be sensitive to ischemia. The device is capable of two-way communication 106 with an external device 107 for notification of the patient 108 of changes in disease state or for communication of diagnostic information to medical personnel or other parties. A standard right atrial lead 109 of a conventional pacemaker is optionally included.

The external programmable unit 107 comprises means for displaying status of implant or historical sensor readings (from data memory storage) 113 and may comprise 114 means for programming internal device via an external interface.

The operable connection 102 between the sensor and the MA element can be delivered into the right-ventricular apex 104 or other location in a similar way as is done with current implanted rhythm-management devices such as pacemakers, defibrillators, and cardioverters, the operation of such delivery devices being known in the art. The current device may also supply these rhythm-management functions, with additional leads, sensors, and electronics as necessary for that purpose. Data from the measurement sensors may be used to aid in the function of such an integrated therapeutic device; for example, the period and vigor of motion of the ventricular apex can be used to detect and differentiate sinus rhythm, ventricular tachycardia, ventricular fibrillation, supraventricular tachycardias, or any other rhythm dysfunction.

A dedicated reference sensor can be omitted when multiple measurement sensors are used, if relative measures between sensing elements (e.g., contractility or differential twist) are sufficient. The reference sensor may also be unnecessary in cases where active sensing is initiated in some way by the patient, because the patient can remain appropriately still during such an examination. Alternatively, the function of the reference sensor may be replaced by filtering or processing of the sensor output such that only physiologically relevant signals are retained. Such a filter may be a conventional high-pass, low-pass, bandpass, or notch filter, or may be adaptive or learning using techniques that are known in the art.

RF or ultrasonic sensor elements can also be used to generate similar diagnostic information. One or more sensors may generate electromagnetic or acoustic waves, and the time and/or amplitude and/or phase of the signal received by sensors at other locations can be used to determine inter-sensor distance. Use of different transmission frequencies, orthogonal ID codes, or other anti-collision methods for different sensor elements allows discrimination of a number of simultaneous signals received from multiple sensors. This approach could also benefit from one or more reference sensors external to the heart, in order to detect absolute motion of the heart within the chest. If the sensors generate and receive waves with spatially non-uniform magnitude and/or phase profiles, the orientation of transmission and reception sensors with respect to each other may also be deduced. The use of multiple co-located sensors oriented orthogonally (or non-coaxially) to one another may facilitate this orientation sensing by providing multiple signals from which relative signal strengths and relative phases may be calculated.

Reflection-mode ultrasound can also be used to interrogate the surface of the ventricle. Such transducers could generate a reflected intensity profile (A-mode scan) that can be analyzed to determine parameters such as the distance between ventricle walls. Analysis of these signals over time can provide diagnostic information about cardiac output and ejection fraction. Alternatively, a sector scan (B-mode image) can be produced and transmitted 106 to the external device 107 for analysis by trained medical personnel.

Figures 2A, 2B:
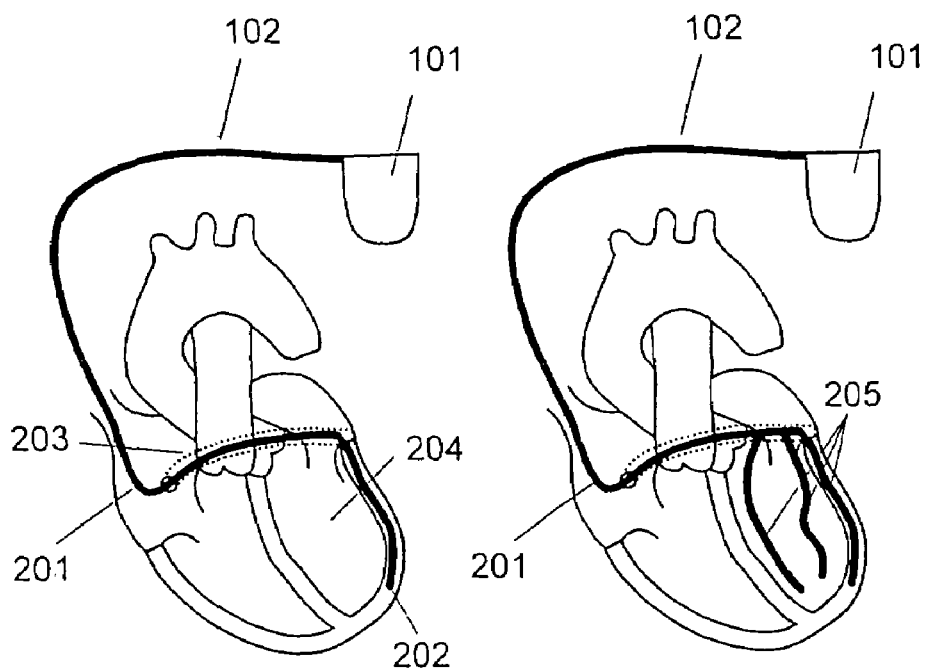
FIG. 2 illustrates three alternative embodiments of the device as implanted in the heart in cross-sectional view, with sensor and lead locations (a) in the proximal anterior interventricular vein, (b) in a plurality of locations spanning the ventricle, and (c) in locations similar to those used in bi-ventricular pacing devices.

Alternatives to this preferred embodiment are depicted in FIG. 2, where in FIG. 2(a) the lead 201 is positioned near the ventricular apex 202 by accessing the cardiac veins via the coronary sinus 203. This placement may be elected over the embodiment of FIG. 1 because of its epicardial lead placement that is in closer proximity to the left ventricle 204. This lead placement may optimally be through the AIV, with the lead advanced as far into that vein as is possible given the gage of the device. Lead placement through the coronary sinus and lead affixation within the venous anatomy are accomplished using methods developed for bi-ventricular pacemakers, and are known in the art. Additional sensors may be placed at intervals along the lead 201 to provide regional information or reference data. In FIG. 2(b), multiple leads 205 are deployed at locations spanning the ventricle in order to provide localized information about disease state. The multiple leads 205 may be fully distinct leads, or they may be portions of a single branched lead 201 as shown.

Deployment of a branched lead structure may be accomplished by having additional branches initially contained within a main lead body, and advanced outside of the lead body only after the lead body is advanced to the appropriate location. Alternatively, the branched structure may be assembled in situ by advancing a first lead to a desired location, then advancing and attaching the branched portions of the lead in a further step.

Figure 2C:
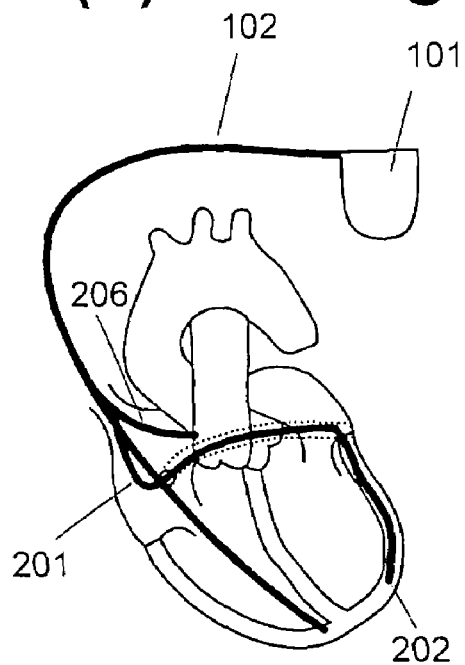

In FIG. 2(c), the device is configured similarly to a current bi-ventricular pacemaker or intracardiac defibrillator, with leads in the right ventricle, right atrium 206, and a proximal cardiac vein 202. This arrangement allows data collection from sensors in each of these locations, wherein the additional atrial sensor 204 may be used as a relatively stable reference, or may be used to detect and distinguish supraventricular tachycardias including atrial fibrillation, or both. Sensors at both the right ventricular apex and cardiac vein can be used to increase position accuracy of an apical measurement, or may be used differentially to determine apical twist or apical contractility, for example. Any of the configurations described here may also deliver therapy, including cardiac pacing, cardioversion, defibrillation, and/or local drug delivery.

Figure 3:
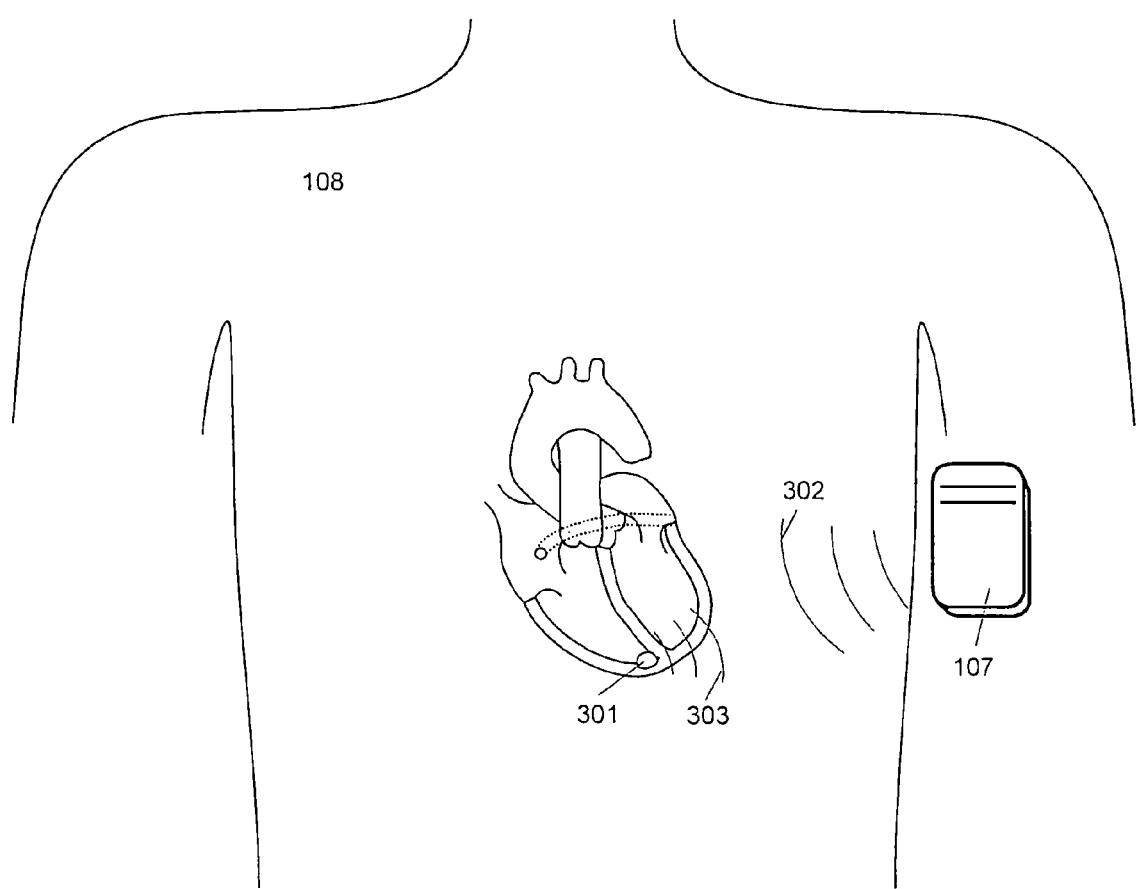
FIG. 3 is a cross-sectional view of the chest and heart including a preferred embodiment of the leadless device with integrated sensors and means for communication with an external device.

Another preferred embodiment is shown in FIG. 3, with an entirely intracardiac sensing device 301 deployed at or near the ventricular apex. One or more sensors are incorporated into the sensing device, as well as means for communication 302,303 with a remote device 107, which may be external to the body or implanted subcutaneously. The remote device 107 may notify the patient 108 of their condition or may recommend therapies or modifications of current therapy, or may transmit diagnostic information to medical personnel or to a central repository or database. The fully intracardiac sensing device has several advantages, including reduced thrombogenicity, reduced device cost, ease of implantation during right-heart catheterization, and potential MRI compatibility. The primary drawback of this approach is the limited space for electronics or battery power within such a sensing device 301.

Other configurations of this embodiment are shown in FIG. 4, where in FIG. 4(a) the sensing device 401 is placed through the coronary sinus deep into a cardiac vein such as the anterior interventricular vein. In FIG. 4(b), a plurality of sensing devices 402 may be placed at locations around the ventricle. This placement may be accomplished surgically, by affixation of sensors epicardially, or percutaneously, by advancing sensors to locations within the cardiac veins. Affixation of the sensing devices within the cardiac veins may be accomplished by barbs, corkscrews, or sizing of the device to fill the area of the cardiac vein. A channel may be included in the sensing device to allow venous blood flow in the presence of the device or to allow guidewire usage during placement. In FIG. 4(c), a sensing device is placed near the ventricular apex 301 as before, and an additional sensing device is placed in the right atrium 403; for example, in the right-atrial appendage. This additional sensing device contains one or more sensors that may be used as reference sensors, or may be used as measurement sensors to detect supraventricular tachycardias or other dysfunction localized or manifested in the atria. In FIG. 4(d), a sensing device is placed near the ventricular apex 301 as before, but in this case an additional sensing device 404 is placed in the cardiac veins at or near the coronary sinus. Sensors in this location may be used as a stable reference, or may be used as measurement sensors to detect atrial dysfunction including supraventricular tachycardias, or may be used to assess mitral valve function (including annular dilatation or contraction during the cardiac cycle), or may be used to detect dysfunction in the basal ventricle. This additional sensing device may also provide therapy for mitral regurgitation by constricting the mitral valve annulus in a way that is known in the art.

In any of the described embodiments, additional sensing devices may be adapted to detect other mechanical or electrical parameters. These sensors may or may not be co-located with the motion sensor elements, depending upon the most advantageous position for such measurements. For example, a pressure sensor may be adapted for use in the heart and placed on its own lead in a preferred location within the coronary sinus. Alternatively, electrical sensors may be placed through the coronary sinus to locations on the epicardial ventricle for electrogram sensing.

Figure 5A:
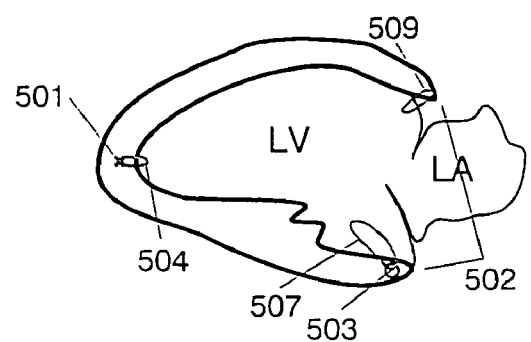
FIG. 5 is a cross-sectional view of the left ventricle and left atrium (a) in a healthy heart and (b) in a heart with an inferior ischemic region, showing the periodic motion of the heart in the chest over the cardiac cycle.
Figure 5B:
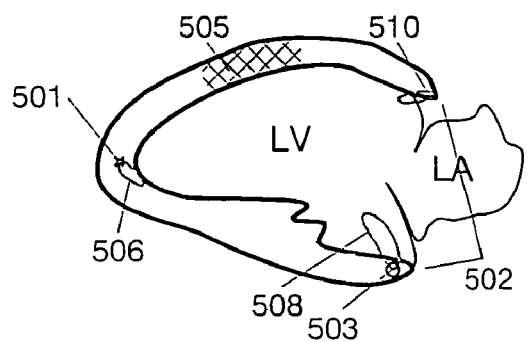

FIG. 5 shows the left ventricle (LV) and left atrium (LA) in a normally functioning heart (FIG. 5(a)) and a heart with an area of acute ischemia (FIG. 5(b)). The apex of the left ventricle 501 floats freely within the chest, and is mechanically the most distant point from the heart's points of attachment at the aorta, pulmonary artery, and great veins, which originate at the basal ventricle 502 near the coronary sinus 503. The apex 501 experiences a periodic motion during the cardiac cycle, then, which is dictated to some degree by the motion and function of all of the heart muscle in the ventricle (being between the point of attachment and the apex). In a normal heart, this motion 504 is roughly directed along the long axis of the ventricle, and is relatively stable over time and across individuals. In addition to a linear motion, the apex also experiences a significant twisting motion during the cardiac cycle in a normal heart, typically of more than 20 degrees.

In a heart with an area of acute ischemia, such as the inferior region 505 indicated in FIG. 5(b), the motion of the apex 506 can change significantly. The spatial orientation and magnitude of this excursion can be significantly different in the ischemic heart, regardless of the location of the ischemia. In fact, the direction of deflection of the apex can indicate the location of the ischemia because the motion path deflects away from the location of the ischemia during contraction. In the example of FIG. 5(b), the motion path 506 is deflected away from the inferior wall compared with the normal motion 504 because of the inferior location of the ischemia.

Figure 13:
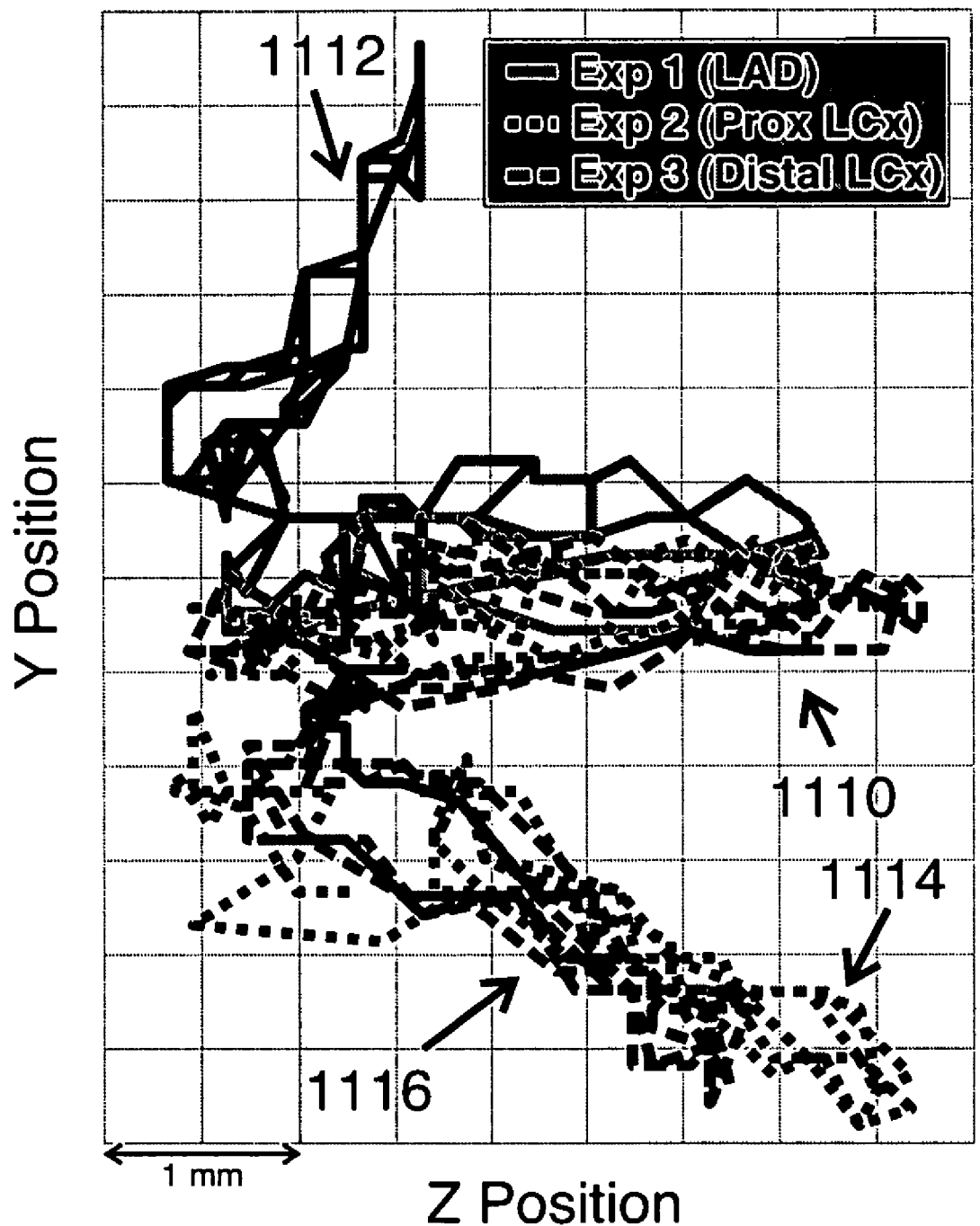
FIG. 13 is a graph of heart apex position before and after occlusion derived from animal experiments.

The graph of FIG. 13 demonstrates this effect in living animals, pigs, whose coronary arteries were surgically ligated and the resulting changes in apical motion were recorded. For consistency, the z axis was aligned with the long axis of the animal's ventricle, and the y axis was chosen to lie in the sagittal plane (thereby matching the anterior/posterior axis relative to the heart). In each of the three animal experiments shown, the apical motion under normal conditions 1110 was similar in extent and direction. During occlusion of the LAD coronary artery 1112, the direction of motion changed significantly, deflecting spatially in a direction away from the affected myocardium. The amplitude of motion was relatively unchanged. During occlusion of the circumflex coronary artery (1114 & 1116), the direction of motion again changed significantly, this time in a different direction, again being directed away from the affected myocardium. The deflection observed was similar for occlusion of either a proximal segment of the circumflex artery 1114 or occlusion of a distal circumflex segment 1116.

Additionally, the extent of apical twist decreases dramatically and immediately under acute ischemia. Therefore, detection of apex motion and twist can be used to remotely detect acute ischemia throughout the ventricle. Similarly, conduction abnormalities within the heart are most pronounced in measurements acquired at the ventricular apex.

Heart rate can easily be determined by the cyclic nature of apical excursion, and ventricular tachycardia and ventricular fibrillation can be identified and distinguished by the characteristic changes that they manifest in apical twist and motion. Supraventricular tachycardias may also be visible at the apex because of the sensitivity of the apex to events within remote regions of the heart. Cardiac overload can also be detected as a change in mechanical vigor of heart contraction. The motion of the coronary sinus 503 in a normal heart 507 and an acutely ischemic heart 508, as well as the motion of the inferobasal ventricle in a normal 509 and acutely ischemic 510 heart, are not as significantly affected by ischemia, though they may be useful for ischemia measurement, and may be especially sensitive to basal ischemia. To detect apical motions, potential locations for the device or leads include but are not limited to the left-ventricular apex, right-ventricular apex, coronary sinus, anterior interventricular vein, cardiac veins, coronary arteries, epicardial apex, esophagus, airway, and pericardial space.

Figure 6A:
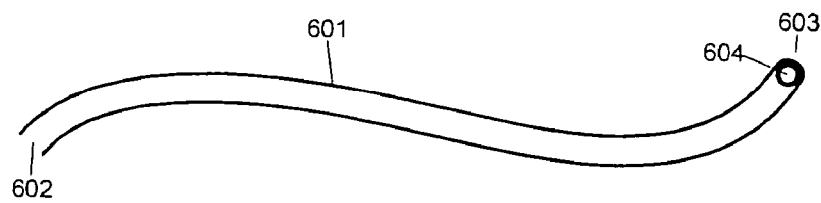
FIG. 6 illustrates five potential configurations of sensors within the body of a lead, with either (a) a localized sensor at the distal lead end, (b) a plurality of localized sensors at different positions along the lead, (c) an extended sensor at or near the end of the lead, (d) sensors at a plurality of lead ends, and (e) an extended sensor spanning a plurality of lead ends.

FIG. 6 shows a cross-sectional view of a sensor lead 601 with proximal end 602 and distal end 603. In FIG. 6(a), a localized sensing device 604 is placed at or near the distal end of the lead. In the embodiment of FIG. 6(b), localized sensing devices 605 are spaced at intervals along the lead body; these allow for local sensing of myocardial parameters. In FIG. 6(c), an extended sensing device 606 is placed at or near the tip of the lead in order to detect tip deflection or torsion over time. Such a sensing device has the advantage of being self-referencing; that is, it inherently measures the differential motion of the lead tip with respect to a more proximal location in the lead, thereby eliminating the need for a reference sensor. In FIGS. 6(d) and 6(e), a branched lead is used with multiple distal ends 607. This branched lead may be deployed in multiple cardiac veins as depicted in FIG. 2(b), or may simply be a variation on another device such as the one depicted in FIG. 1, wherein the right-ventricular lead tip 104 may alternatively branch and be affixed into multiple locations within the ventricle wall. Such an affixation mechanism would have a lower likelihood of dislodgement, and could be used to measure local contractility at the apex. FIG. 6(d) depicts such a branched lead with individual localized sensing devices 608 at or near the tip of each lead. In FIG. 6(e), an extended sensing device 609 spanning a plurality of branches is used, wherein sensing of the relative motion between lead tips is inherently measured.

Passive or active sensors may also be used in a leadless configuration, wherein one or more sensing devices are implanted at various locations in the heart. FIG. 7 illustrates several potential sensor configurations within such an implanted sensing device. In FIG. 7(a), the sensing device 701 contains a plurality of sensors 702-704, each having different sensitivities. If accelerometry or directional RF sensing is used, then the multiple devices may sense multiple axes of motion. As illustrated here, three orthogonally oriented sensors may be used to provide six-degree-of-freedom information about the location of the sensing device. Multiple sensor types, such as accelerometry and RF sensing, or RF sensing and EKG sensing, may also be used together in such a sensing device. In FIG. 7(b), a single sensor 705 is contained within the sensing device 701. This has the advantage of simplicity and reduced size. In FIG. 7(c), an extended sensing device 706 may also be used, with localized sensing components 709, 710 located at locations along the extended sensing device including its ends 707,708. The localized sensor components 709, 710 may be in any configuration possible for a localized sensor device, including those shown in FIG. 7(a) or 7(b). In FIG. 7(d), the extended sensing device 706 contains an extended sensor 711, which may detect bending, twisting, compression, or other differential loads on the extended implant 706, and may detect absolute motion of the extended sensing device 706 as well. A remote device (e.g., 107), either external or implanted, can communicate with any of these sensing devices, and their position, acceleration, rotation, or other sensed information may be gathered in that way. Also, though the preferred embodiment is a continuous monitor, the remote device may also be used only intermittently, with analysis of cardiac dysfunction occurring only at specified time intervals, when the patient is in the proximity of a remote-sensing station, or when the patient or medical professional explicitly desires diagnostic information.

For the leadless embodiments discussed above, means for communication between the sensing device(s) and a remote device is necessary. A preferred embodiment of this communication means is through passive inductive coupling of the sensing device with a powered remote device. The implanted sensing device would then use a coil or other antenna for reception of radiofrequency signals from the remote device. These radiofrequency signals could be used to energize circuitry that makes a particular measurement, which could then be transmitted back to the remote device via the same antenna as was used for signal reception, or via a second antenna. Alternatively, the reception antenna itself may be structured in such a way that sensing is integrated with the transmission means. Four such approaches are depicted in the circuit diagrams of FIG. 8. In FIG. 8(a), a simple tuned LC circuit 801 forms the entire implanted sensor. Inductor 802 and capacitor 803 values are chosen to provide a resonant frequency in the radiofrequency range, with sufficient tissue-penetrating ability to communicate with the remote device. In this arrangement, the distance and orientation between the implanted sensing device and the remote device can be determined by the amplitude and/or phase of echoes received by the remote coil in response to a continuous-wave or pulsed stimulus.

Multiple orthogonally oriented coils of this type within the sensing device may be used to decouple three-dimensional sensing-device orientation (relative to the transmitted field) from amplitude and phase measurements; multiple external coils may be used to determine three-dimensional position based upon triangulation methodology known in the art. In this case, the remote device must contain one or more excitation antennae, which may be of the solenoid or Helmholtz type. In FIG. 8(b), a similar resonant structure is employed, but with a variable capacitor 804 used in this case. The variable capacitor may be actuated by acceleration (as is the case in certain MEMS accelerometers), angular rate of rotation, fluid pressure, electrical activity, or any other desired measurement. Variations in this capacitance translate to variations in the resonant frequency of the implanted sensing circuit, which can be detected externally. A swept-frequency or broadband pulse applied at the remote device produces return signals that can be processed to determine the resonant frequency, and thereby capacitance, of the implanted sensing circuit, using any of a variety of techniques including peak detection, FM demodulation, Fourier transform methods, filter banks, and the like.

Figure 8C:
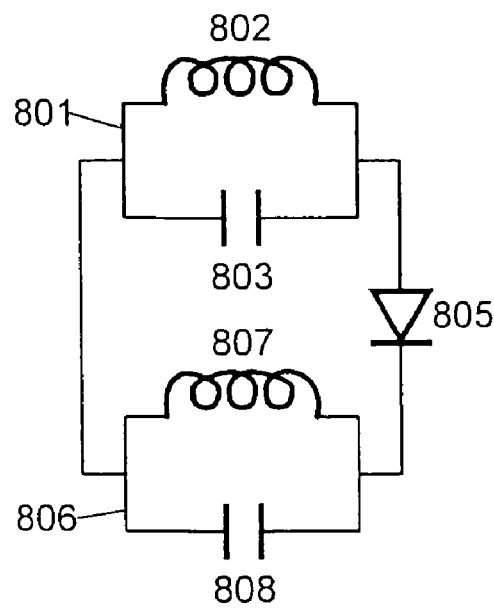
FIG. 8 illustrates schematic diagrams of four potential electromagnetic sensors, including (a) a parallel resonant circuit, (b) a parallel resonant circuit with variable capacitance, (c) a plurality of parallel resonant circuits with nonlinear coupling, and (d) a parallel resonant circuit with microchip or RFID modulation.

A similar result could be obtained by using a variable inductance in lieu of the variable capacitor; such a circuit might comprise a flexible or compressible coil whose inductance changes can be calculated as a function of structural changes. In FIG. 8(c), a dual-resonant circuit is presented, with first resonant circuit 801 as in (a), connected as shown with a nonlinear element 805 and a second resonant circuit 806. The nonlinear element 805 may be a diode or any other nonlinear circuit (preferably passive), such as a full-wave rectifier, frequency doubler, squaring circuit, absolute-value circuit, etc. The nonlinear element produces additional frequency content in the signal transmitted by the remote device and received by the first resonant circuit 801.

Figure 8D:
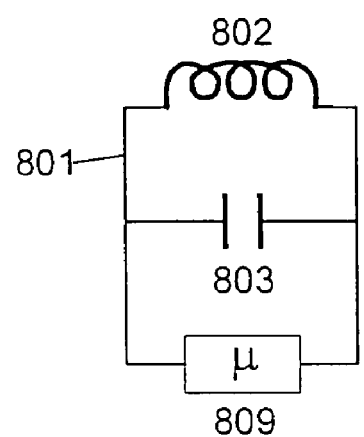

The second resonant circuit 806 is designed to resonate at one of these harmonic frequencies generated by the nonlinear element, thereby generating a unique signature that can be received at the remote device and that is not susceptible to interference from the originally transmitted signal. The inductor 807 or capacitor 808 in this second resonant circuit 806 may be variable as discussed above, to provide additional physiologic information to the remote device. In FIG. 8(d), a final circuit is proposed, with resonant portion 801 as described above, connected in series or parallel (as shown) with a microchip 809 capable of performing RFID functions, for example the Philips Semiconductor SL1ICS3001U. The inclusion of such a chip allows unique identification of multiple resonant circuits, if present, and provides anti-collision capabilities such that each tag may be individually interrogated. This structure also may be used to store information about the implanted sensing device's most recent interrogation, the state of the heart at that time, and other diagnostically relevant data. If RFID-like technologies are not employed, then multiple implanted sensors may be differentiated by their different frequencies of operation, or by Wiegand-wire identification, or similar methods.

Figure 9:
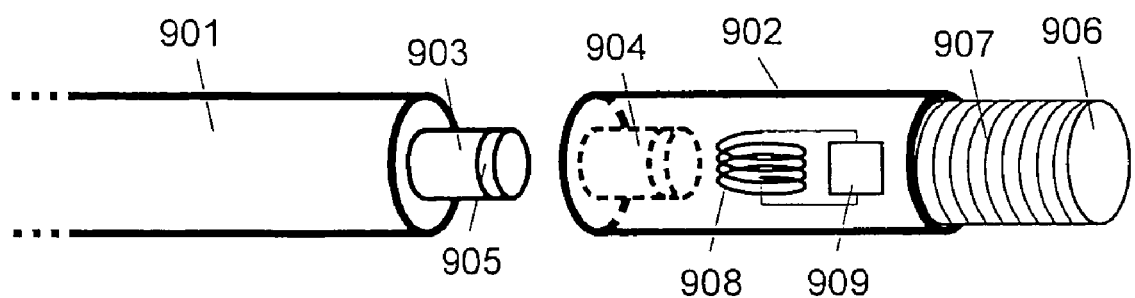
FIG. 9 is a schematic view of a preferred embodiment of the delivery device for a leadless embodiment of the invention.

A potential delivery apparatus for a leadless sensing device is shown in FIG. 9, where a deployment catheter 901 is advanced through the venous or arterial anatomy to the desired deployment location. The deployment catheter body 901 includes at its distal end a detachable portion 902 where the catheter body 901 and detachable component 902 are connected by affixation structures 903, 904 on each piece, with detachment mechanism 905 that can be actuated at the proximal end of the catheter body (not shown). The detachable portion of the catheter body includes a mechanism 906 for anchoring of the detachable portion 902 into the myocardium or vessel, which may be a threaded screw 907, helical corkscrew, barbs, cement, epoxy, adhesive, suture, or other affixation mechanism.

This mechanism may be passive, actuated simply by applying torque or pressure at the proximal end of the catheter body, or may be engaged by a mechanism that can be actuated at the proximal end of the catheter body independently or when the detachment mechanism 905 is actuated. Housed within the detachable portion 902 is a circuit for measurement and communication, with at least a communication element such as an RF coil 908. Additional sensing circuitry 909 may be connected to this communication device, for example in any of the configurations as depicted in FIG. 8. Any number of sensor elements may be contained within this lead body, and modifications to this design may be easily conceived to provide any of the sensor configurations as depicted in FIG. 7. For space savings, the RF coil (if used) may be incorporated into the outer sheath of the detachable portion, or may be integrated with the anchoring mechanism 907. A single catheter body 901 may be equipable with multiple detachable portions 902 for rapid deployment of multiple implanted sensors. The detachable portion can potentially be recaptured and removed at a later time by re-engaging the detachment mechanism 905 with a similar catheter body 901. A similar delivery device could also be used intra-operatively or through a minimally invasive transthoracic procedure, with the catheter body 901 replaced by a handheld deployment device or gun.

Deployment of the embodiments that include leads can be accomplished through similar apparatus, without the need for detachment mechanisms 903-905. Delivery of leads of the same general structure has been well described in the art for application in implantable pacemakers and defibrillators. Embodiments of the device may also be delivered epicardially through a minimally invasive tool that does not require open surgery.

Once signals are collected using one or a combination of sensor types, information must be processed in order to detect acute events or provide diagnostic information to medical personnel. Processing may be in the form of waveform vs. time analysis, where the collected information is analyzed temporally to detect an event. Measured parameters may vary with the cardiac cycle, so heart rate information may be derived from the measured parameter, and then potentially used to register portions of the acquired data from multiple heartbeats. Collected information can also be analyzed by frequency content by using FM demodulation or a Fourier or similar transformation to synthesize frequency-domain information from the collected signal. Collected data may also be analyzed using a matrix computation with a parameterized model of expected sensor behavior in normal and dysfunctional states. Such an approach could result in a statistically optimized determination of cardiac dysfunction. Processing may also involve use of multiple parameters derived from different sensor types analyzed using any of the available multi-parameter techniques.

The device may also deliver therapies to the patient as appropriate for the disease state diagnosed. If acute ischemia is diagnosed, anticoagulants, antiplatelet agents, thrombolytic drugs, or therapeutic ultrasonic or RF energy could be immediately administered in addition to notification of the patient. For rhythm disturbances, antiarrhythmic agents or electrical defibrillation, cardiversion or pacing shocks could be applied. For symptoms of congestive heart failure or cardiomyopathy, diuretics, inotropic agents, or other therapies could be administered or adjusted using information derived from the device. Therapeutic acoustic energy or nerve stimulation could also be administered when indicated. Medical personnel may program parameters relating to the administration of these therapies into the device, so that the appropriate level of therapy is administered to each patient.

Any or all aspects of this invention (e.g., one or more of the subject sensors) may be integrated into existing implanted devices to provide additional diagnostic capabilities to these devices. Many such devices, such as pacemakers, implanted defibrillators, cardioverters, ventricular assist devices, infusion pumps, implantable event monitors (which typically record EKG or other cardiac diagnostic information over an extended period of time), annuloplasty rings, and atrial-appendage occlusion devices, treat or measure only a single dysfunction in the patient, even though recipients of these implants are at high risk of cardiac events in addition to their primary dysfunction. For example, an accelerometer sensor may be integrated into a lead of an ICD. This invention may also be integrated into catheter-based therapies for use during cardiovascular intervention. Another advantage of integrating the subject sensors with other diagnostic and/or therapeutic devices is the reduction in the number of implant procedures and the time in which it takes to perform such which in turn is beneficial to the patient and reduces costs. The remote or external device (e.g., 107) can take a number of forms depending upon the need for accuracy and robustness of information, the desire for continuous monitoring, and other considerations. In the preferred embodiment, the remote device consists of a RF coil capable of data communication with a subcutaneous MA element, said coil being placed on the chest of the patient at the time of clinical examination or in the patient's home. This coil would read data from the MA element's RAM storage and relay the information to a processor in the remote device to provide detailed feedback to the patient or medical personnel pertaining to their condition. The remote device could also be used to calculate and transmit thresholds and other parameters to the memory in the MA element for improved ischemia detection and discrimination.

In another embodiment of the remote device, a robust remote device consists of a number of interrogation coils that are placed around the patient's chest via a wrap or other wearable apparatus for placing coils on the chest in a relatively stable configuration. The coils themselves may sense their positions relative to each other, with enough coils provided that each coil's location can be triangulated using telemetry to and from other external coils. These coils may be used to determine the location of an RF-active implant such as a stent or small coil without the need for an implanted accelerometer or other powered device. The external coils are connected to a demodulation circuit, which converts received signals into information signals representing the sensed physiological property such as acceleration, position, or any other of the aforementioned sensed properties. This sensed property may be digitized for easy transmission (preferably via cable, but alternatively via cellular telephony, wireless-LAN technologies, or other powered telemetry method), and is then sent to a processing unit such as a digital computer, handheld computing device, or application-specific integrated circuit, where the data from the various sensors is processed, interpreted, and/or displayed to provide medical personnel or the patient with information about their cardiac health.

Another embodiment of the remote device includes a smaller number of external interrogation coils, preferably just one, in order to reduce the size of the remote device at the potential expense of diagnostic accuracy. In this embodiment, a wearable wrap is not necessary because the interrogation coil(s) work from a single position on the chest. The interrogation coil(s) are connected as needed to demodulation and digitization circuitry, and the resulting signal is then transmitted to a handheld or other computing device, preferably via cable. The data are then processed and displayed on the handheld remote device for use by the patient or medical personnel. In this embodiment, the entire remote device might be kept in a jacket pocket or other worn location for pseudo-continuous monitoring.

Another alternative embodiment of the remote device is implanted in the body, preferably in a location similar to that used by current event monitors or implantable defibrillator canisters. The remote device may also be implanted within a heart cavity such as the atrial appendage, and may be integrated with one or more sensing or reference sensors. The remote device in this embodiment may communicate information to the patient through an alarm, physiologic response, or via a powered telemetry protocol such as Bluetooth to nearby wireless devices. The remote device in this case may continuously monitor and record information about the patient's state, downloading information to an external location only when the patient comes into contact with an external wireless receiver.

With some of these embodiments, a central data repository may be necessary to store each patient's records and baseline and historical sensing-device signals from each patient, so diagnoses may be made based on changes in the condition of the patient's heart. This may be accomplished by on-board memory in a device with fully implantable remote circuitry, but a central repository may be preferable in devices that rely upon external remote devices so that any remote device can be used with the patient's implant while retaining access to the patient's full medical history.

In one embodiment of the present invention, a method is provided for diagnosing and/or treating cardiac dysfunction, which may include including myocardial ischemia, myocardial infarction, and the like. The method comprises the placement of one or motion detecting sensors at one or more locations near the apex of the heart; operable connection of the one or more sensors to an MA element capable of processing or transmitting the sensed information; analysis of the sensed information to determine the disease state of the heart; communication of information about the disease state to the patient or to medical personnel; and initiation of therapy for the disease state where appropriate. Specific embodiments may include some or all of the above elements, as described above.

The subject methods may be performed using the subject systems and devices or by other means. The methods may comprise the act of providing a suitable device. Such provision may be performed by the end user. In other words, the act of "providing" merely requires the end user obtain, access, approach, position, set-up, activate, power-up or otherwise act to provide the requisite device in the subject method. Methods recited herein may be carried out in any order of the recited events which is logically possible.

It is to be understood that this invention is not limited to the particular methodology, protocols, devices, software, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a device" includes a plurality of such devices and reference to "the sensor" includes reference to one or more sensors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are herein described. Efforts have been made to ensure accuracy with respect to the numbers used but some experimental errors and deviations should be allowed for. Unless otherwise indicated, parts are parts by weight, molecular weight is average molecular weight, temperature is in degrees centigrade; and pressure is at or near atmospheric.

All publications mentioned herein are incorporated herein by reference for all relevant purposes, e.g., the purpose of describing and disclosing, for example, the constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for detecting an ischemic condition in a patient, the method comprising:
    sensing the motion of the ventricular apex of the heart in two or more directional axes with at least one motion sensor implanted at the heart;
    processing signals generated by the at least one motion sensor, the processing comprising relating the signals from two or more directional axes of movement to at least one predetermined baseline value of the movement of the apex of the heart; and
    wherein the location of an ischemic condition of the heart is determined by the deflection of said path that the ventricular apex traverses over time, wherein the deflection is in a direction away from affected myocardium of the heart.

2. The method according to claim 1, wherein the sensing is performed with a single multiple dimensional motion sensor that provides two or three-dimensional measurements.

3. The method according to claim 1, further comprising producing an output, wherein the output is a cardiac pacing signal.

4. The method according to claim 1, further comprising producing an output, wherein the output is the delivery of a therapeutic agent to the heart.

5. The method according to claim 1, further comprising producing an output, wherein the output is an alarm signal produced when a processed signal is determined to be outside a predetermined threshold range.

6. The method according to claim 1, further comprising performing an electrocardiogram of the heart with another sensor.

7. The method according to claim 1, wherein the at least one sensor is implanted endocardially.

8. The method according to claim 1, wherein the at least one sensor is implanted epicardially.

9. The method of claim 1, wherein said at least one motion sensor is a rotational motion sensor.

10. The method of claim 1, wherein the at least one motion sensor is adapted to be sensitive to acceleration in axes perpendicular to the sensor's lead.

11. A method for detecting an ischemic condition in a patient, the method comprising:
    sensing the motion of the ventricular apex of the heart in two or more directional axes with at least one motion sensor implanted at the heart;
    processing signals generated by the at least one motion sensor at apical motion frequencies to 4 Hz, the processing comprising relating the signals from two or more directional axes of movement to at least one predetermined baseline value of the movement of the apex of the heart,
    wherein the location of an ischemic event is determined by the deflection of said path that the ventricular apex traverses over time, wherein the deflection is in a direction away from affected myocardium of the heart.

12. The method of claim 11, wherein the at least one motion sensor is a multiple-dimensional sensor that provides two or three-dimensional measurements.

13. The method of claim 11, wherein said at least one motion sensor comprises a multiple-dimensional sensor that provides two or three-dimensional measurement, and a rotational motion sensor.

14. The method of claim 13, wherein six degrees of motion information are combined for processing.

* * * * *